(12) United States Patent
Baron et al.

(10) Patent No.: US 6,565,752 B1
(45) Date of Patent: May 20, 2003

(54) METHOD FOR SEPARATING A FLUID SUBSTANCE AND DEVICE THEREFOR

(75) Inventors: Gino Baron, Tervuren (BE); Gert Desmet, Elewijt (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

(21) Appl. No.: 09/445,206

(22) PCT Filed: Jun. 3, 1998

(86) PCT No.: PCT/EP98/03485

§ 371 (c)(1),
(2), (4) Date: Mar. 2, 2000

(87) PCT Pub. No.: WO98/55858

PCT Pub. Date: Dec. 10, 1998

(30) Foreign Application Priority Data

Jun. 4, 1997 (EP) .............................................. 97201699

(51) Int. Cl.[7] .............................................. B01D 15/08
(52) U.S. Cl. ........................ 210/635; 210/656; 210/657; 210/660; 210/774; 210/175; 210/198.2; 210/263; 436/177; 436/178; 436/180; 436/161; 422/63; 422/70; 422/101
(58) Field of Search .............................. 210/175, 198.2, 210/359, 511, 634, 635, 656, 748, 767, 774; 209/3, 11, 155, 156, 158; 422/63, 69, 70, 101; 436/161, 166, 174, 180, 177, 178

(56) References Cited

U.S. PATENT DOCUMENTS

| 3,417,548 A | | 12/1968 | Thompson |
| 3,449,938 A | * | 6/1969 | Giddings |
| 3,511,028 A | | 5/1970 | Saylor |
| 4,839,032 A | | 6/1989 | Whitlock ..................... 210/748 |
| 4,874,507 A | | 10/1989 | Whitlock ..................... 209/11 |
| 5,770,087 A | * | 6/1998 | Reuter ..................... 210/198.2 |

FOREIGN PATENT DOCUMENTS

| DE | 4108820 | 9/1992 |
| EP | 0670489 | 9/1995 |
| GB | 1242255 | 8/1971 |

* cited by examiner

Primary Examiner—Joseph W. Drodge
(74) Attorney, Agent, or Firm—Banner & Witcoff, Ltd.

(57) ABSTRACT

The present invention relates to a new separation method and a device therefor, especially to a device and method for chromatographic chemical analysis. In the method according to the invention, the driving of the mobile phase fluid in, through and out the separation channel, said channel being defined by at least two channel elements, is mainly caused by a relative movement of at least one channel element compared to at least one of the other channel elements preferably the movement of the mobile phase fluid and the sample to be separated through the separation channel is sustained by relief elements, such as one or more protrusions, recesses, holes or irregular porous-like structures, which are arranged on at least one of the channel elements.

34 Claims, 24 Drawing Sheets

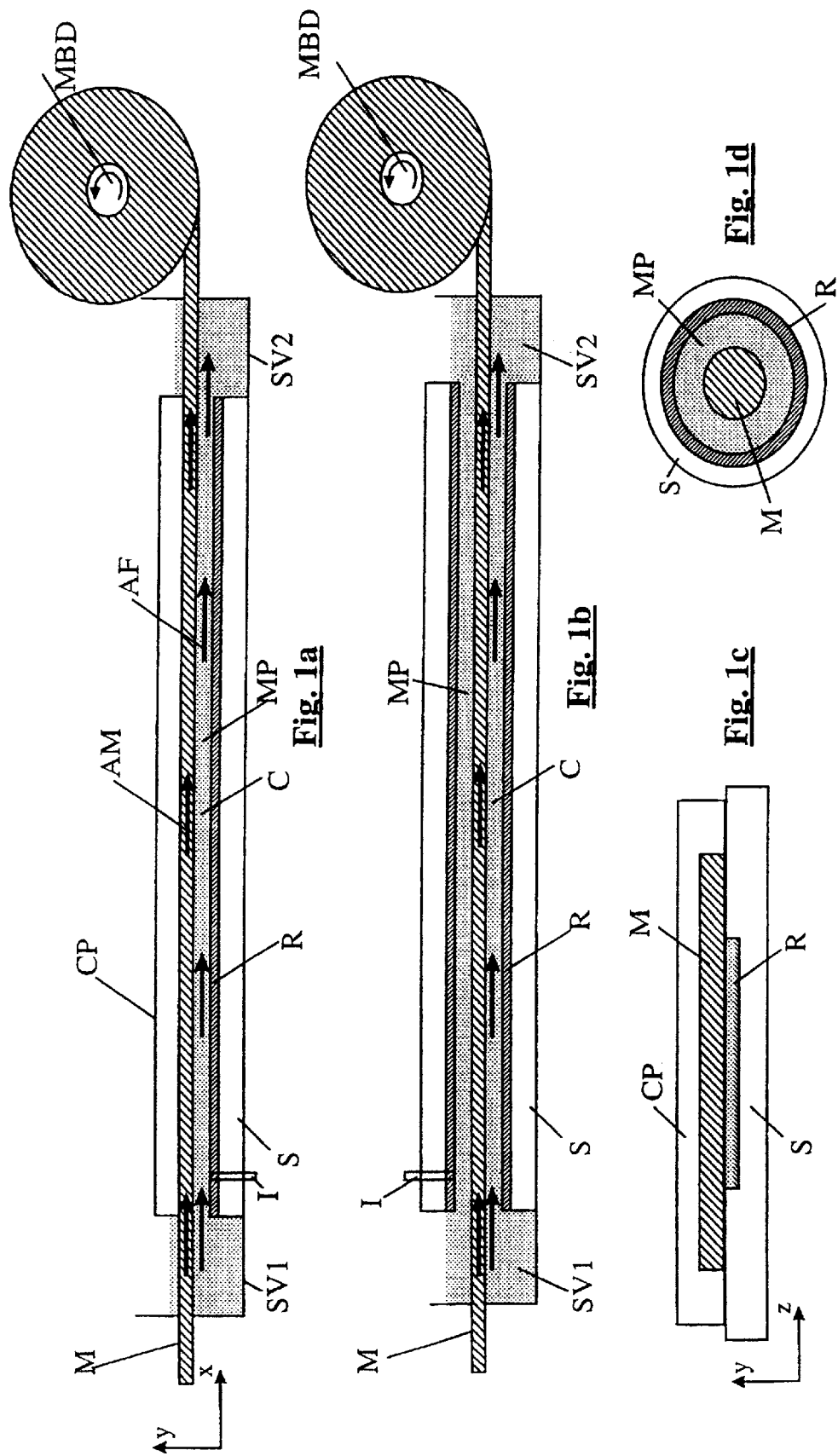

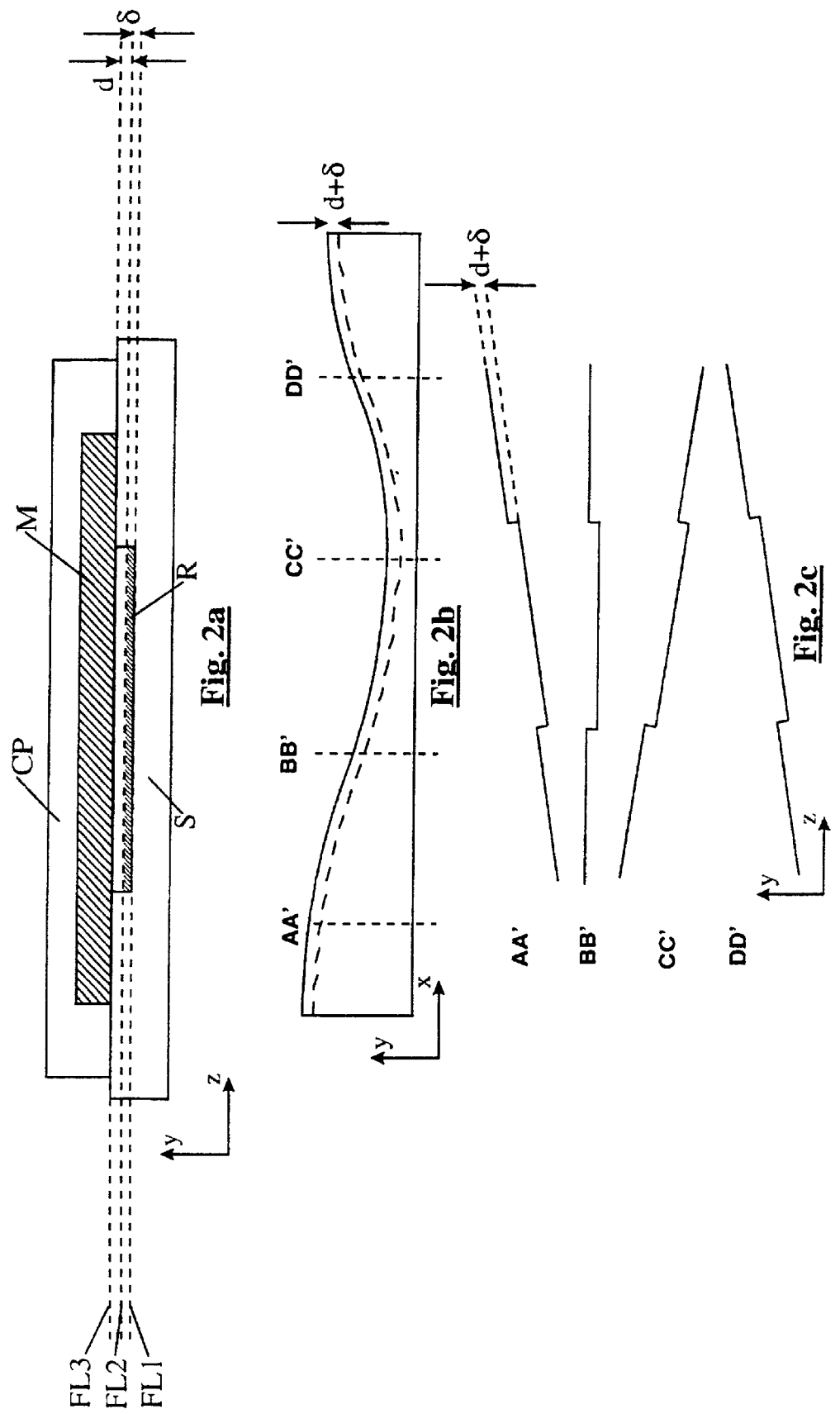

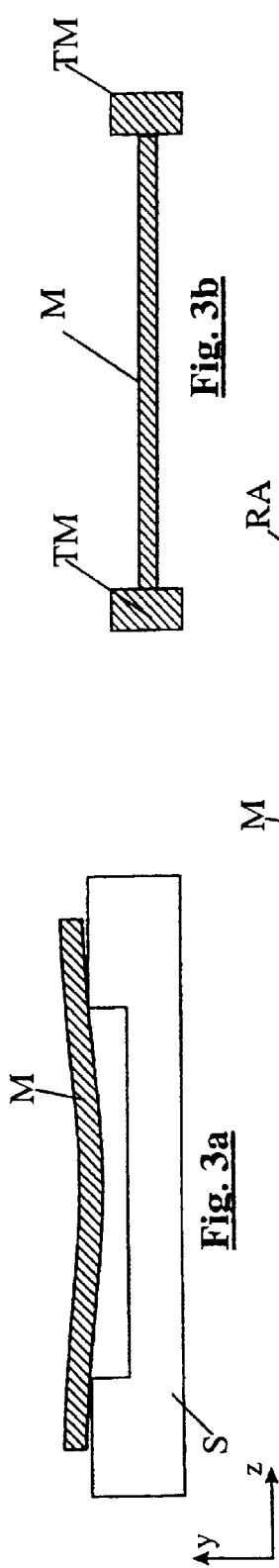
Fig. 3a
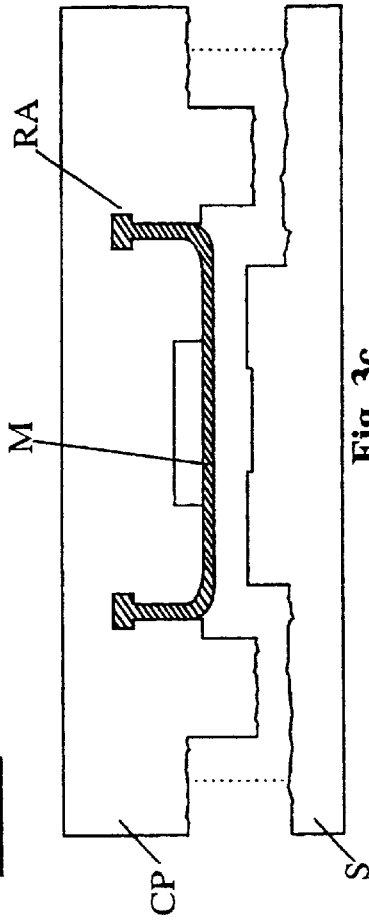
Fig. 3b
Fig. 3c
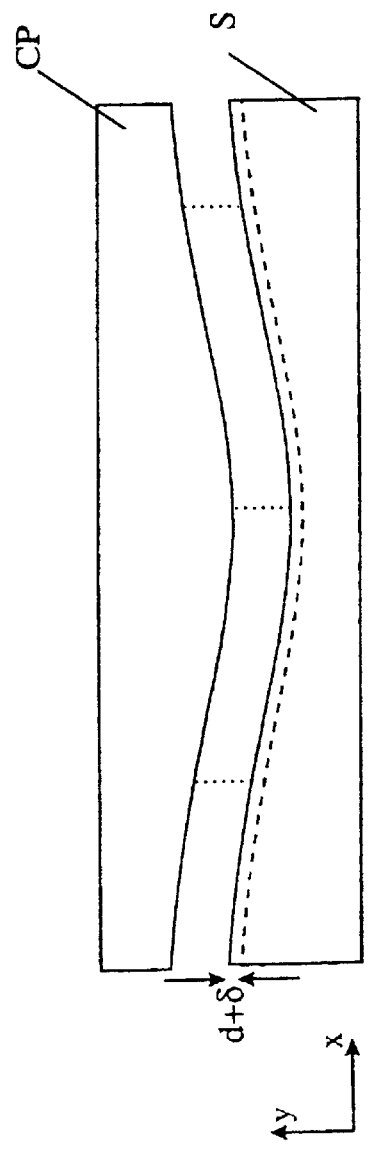
Fig. 4

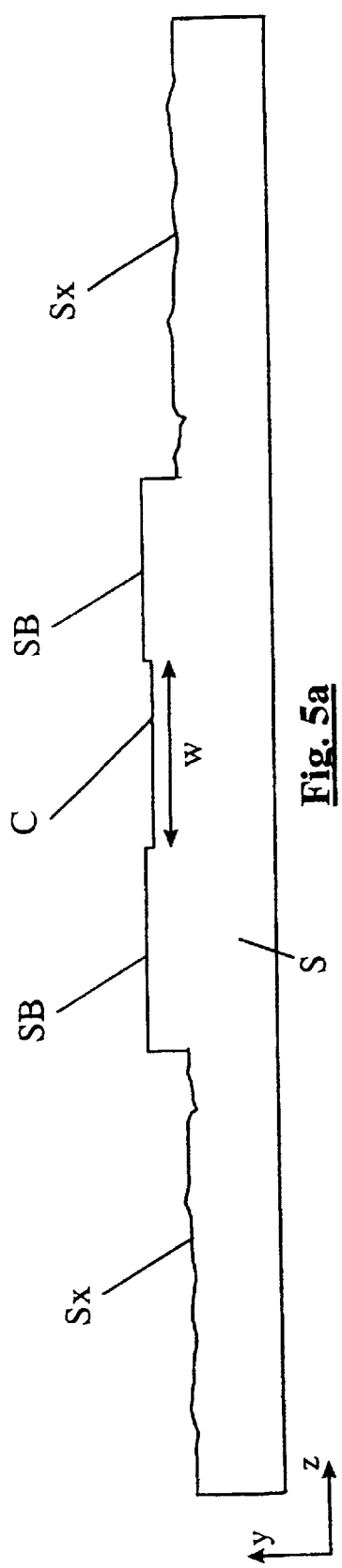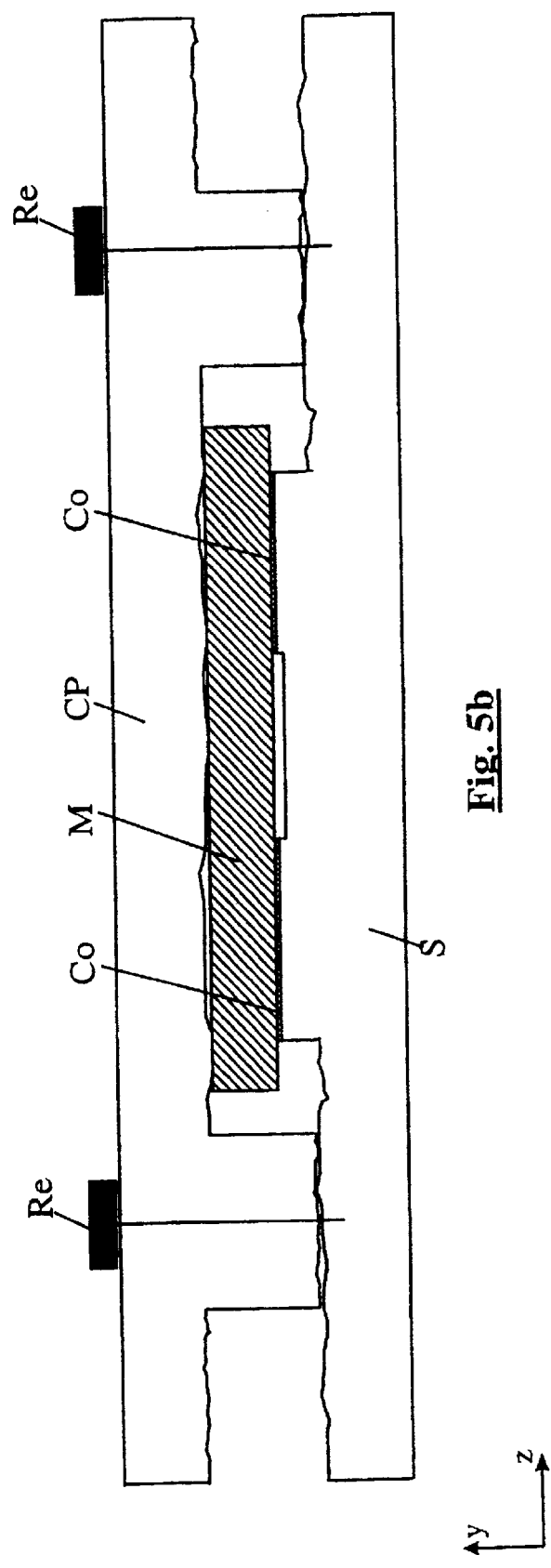

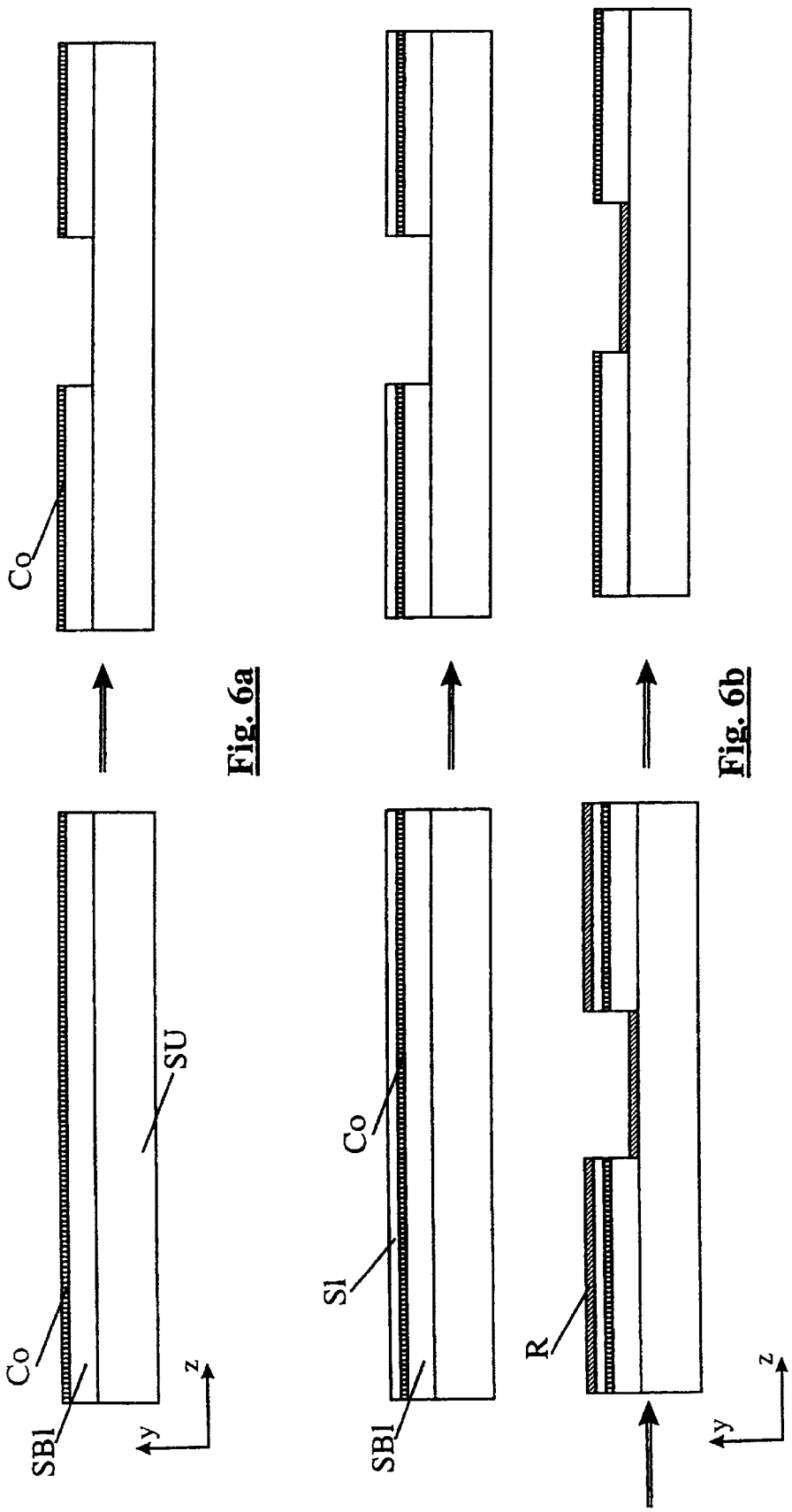

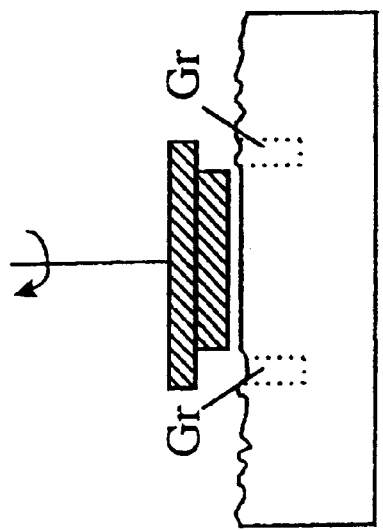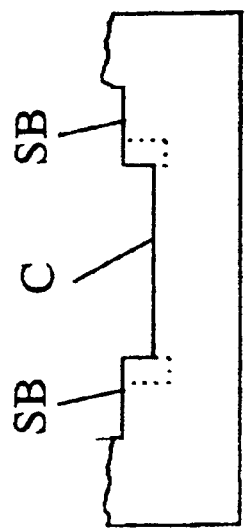
Fig. 7a
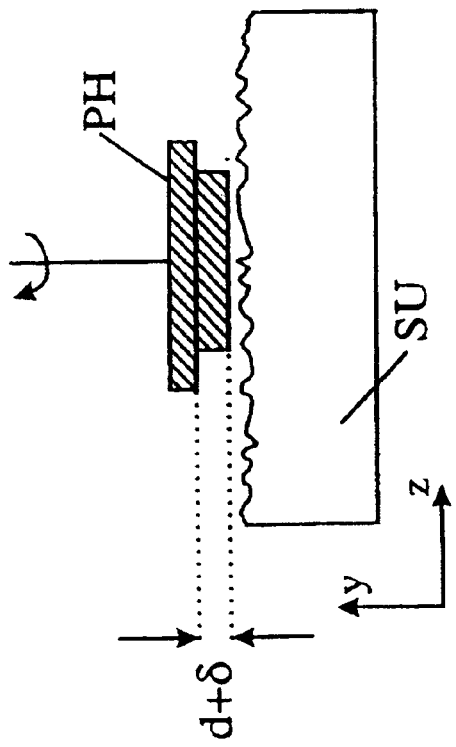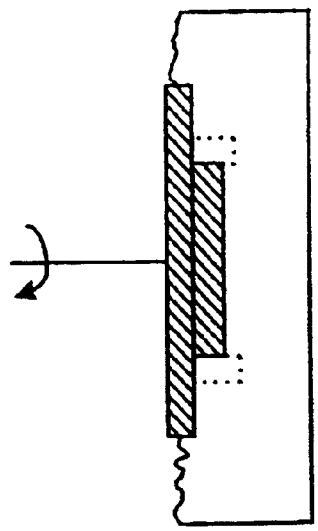
Fig. 7b

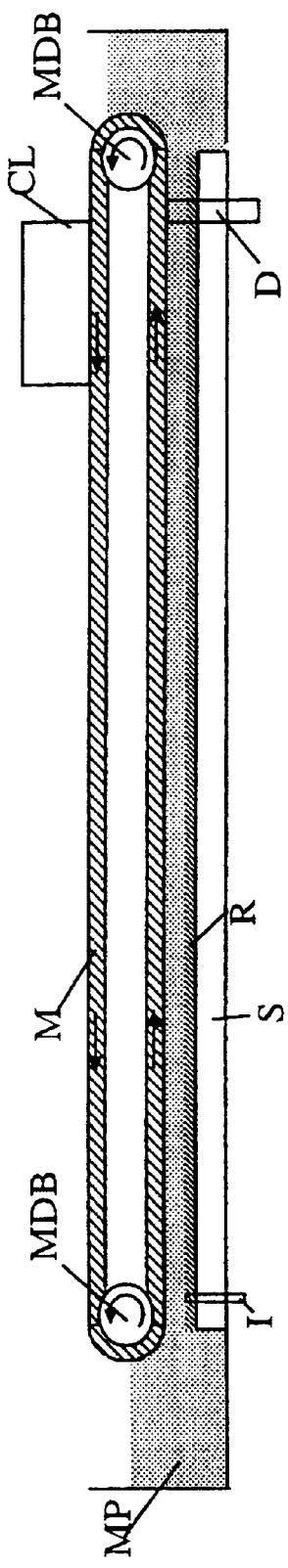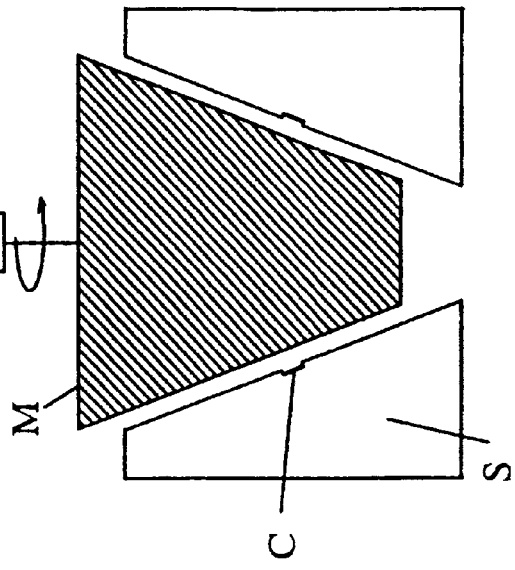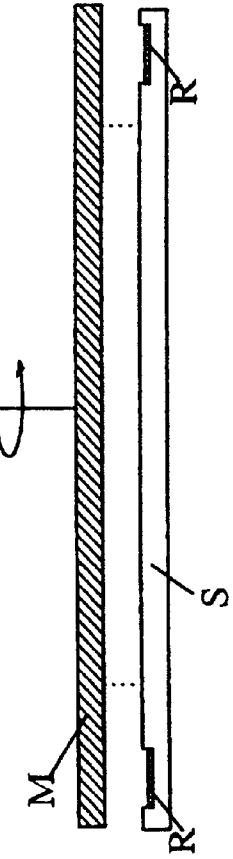
Fig. 11a
Fig. 11b
Fig. 11c

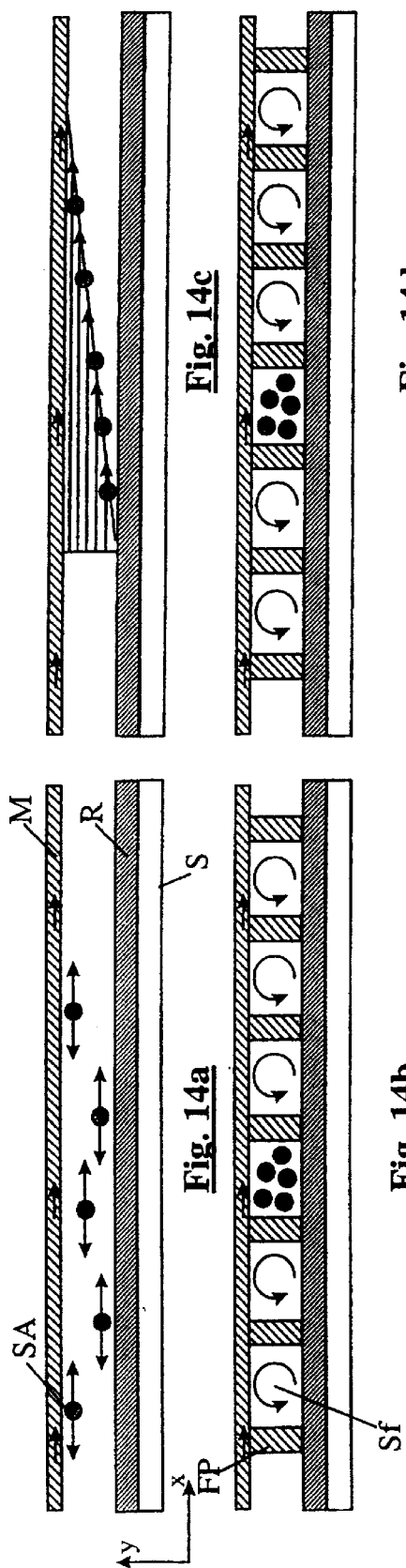
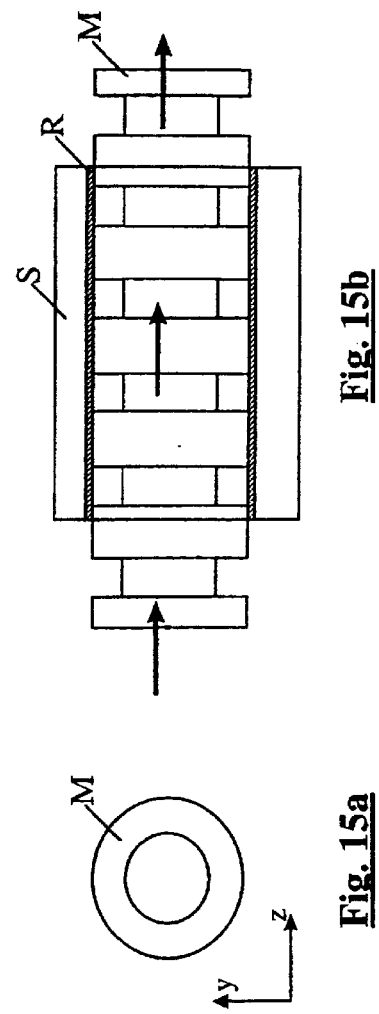
Figure 14. Comparison between open-channel flow (a,c) and compartmentalized flow (b,d): influence of molecular diffusion (a,b) and velocity gradient (c,d).

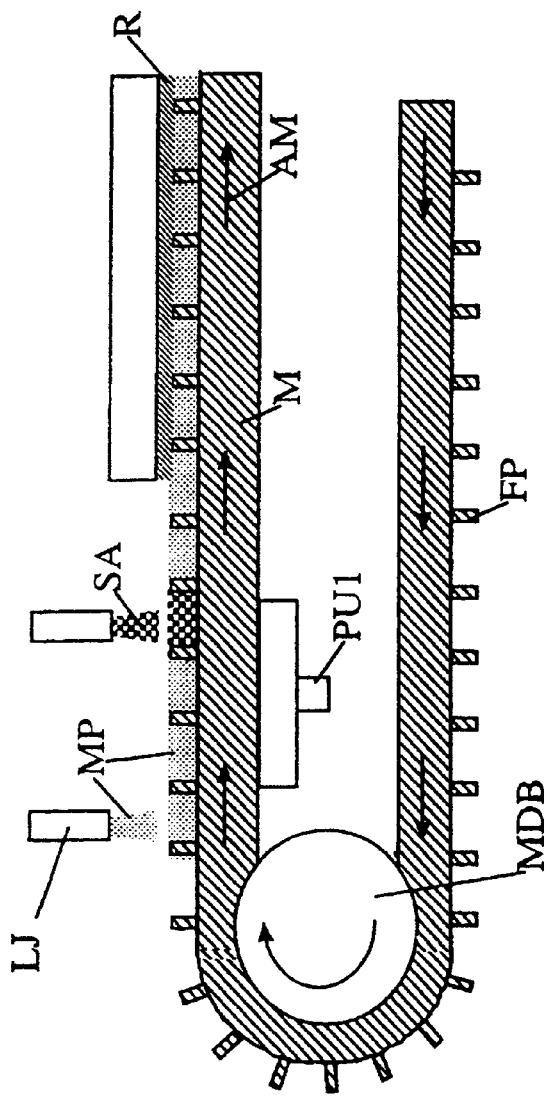
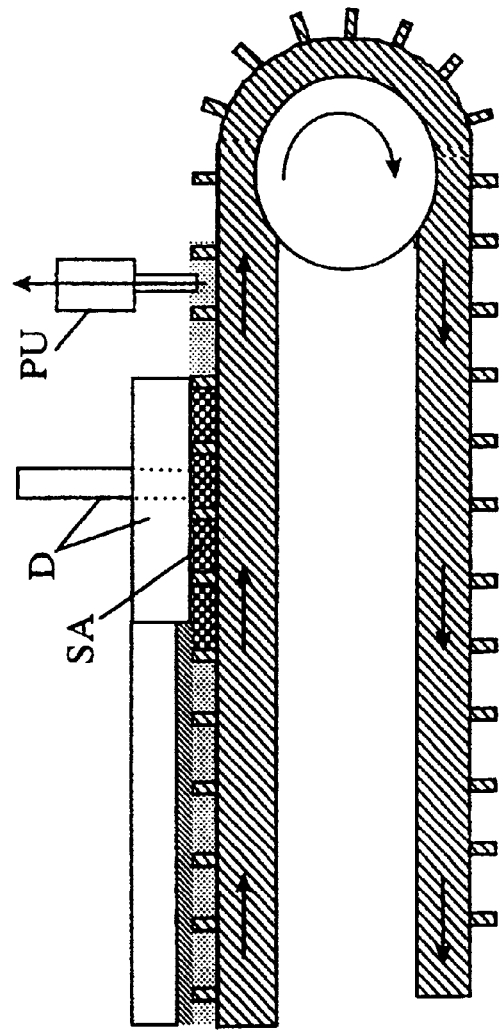
Fig. 16a
Fig. 16b

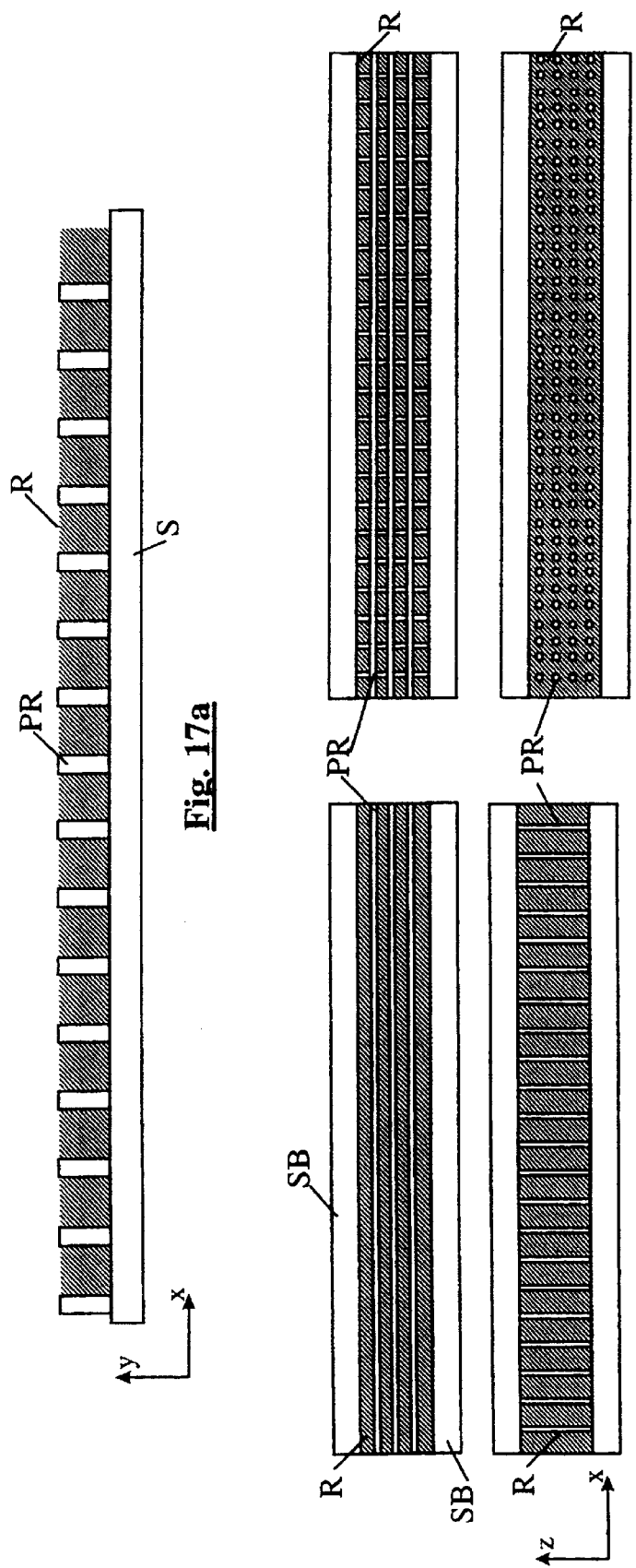

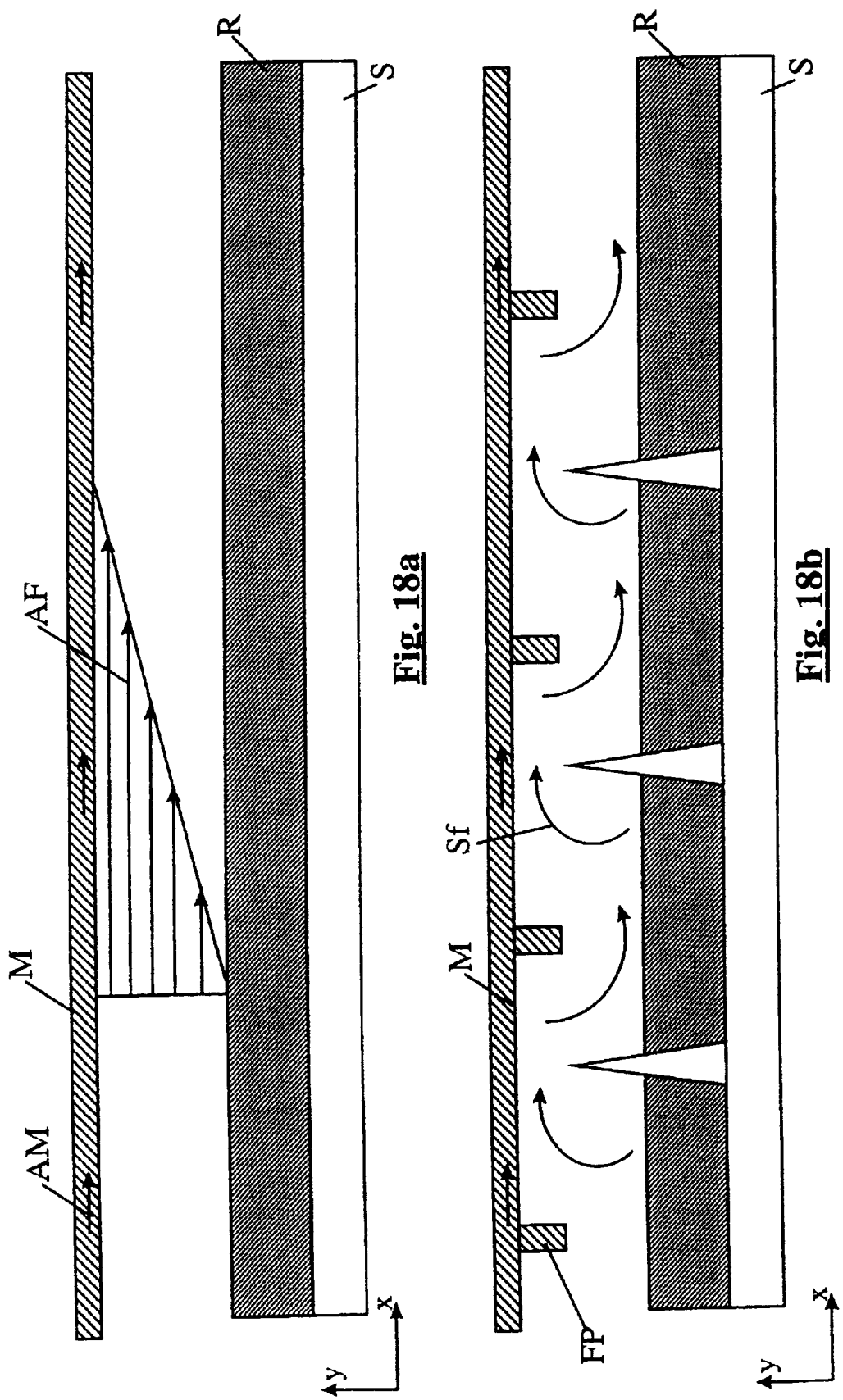

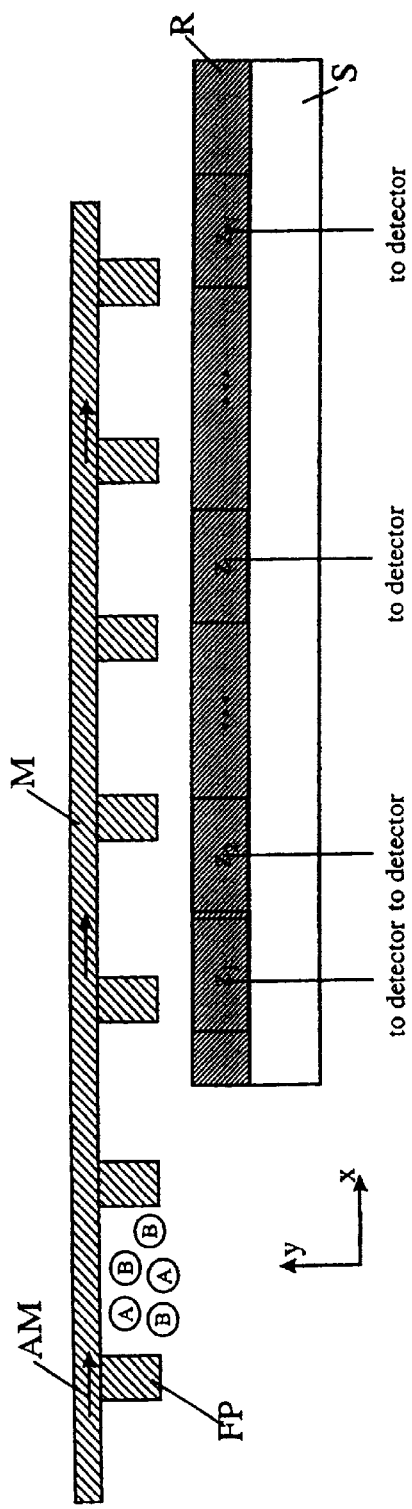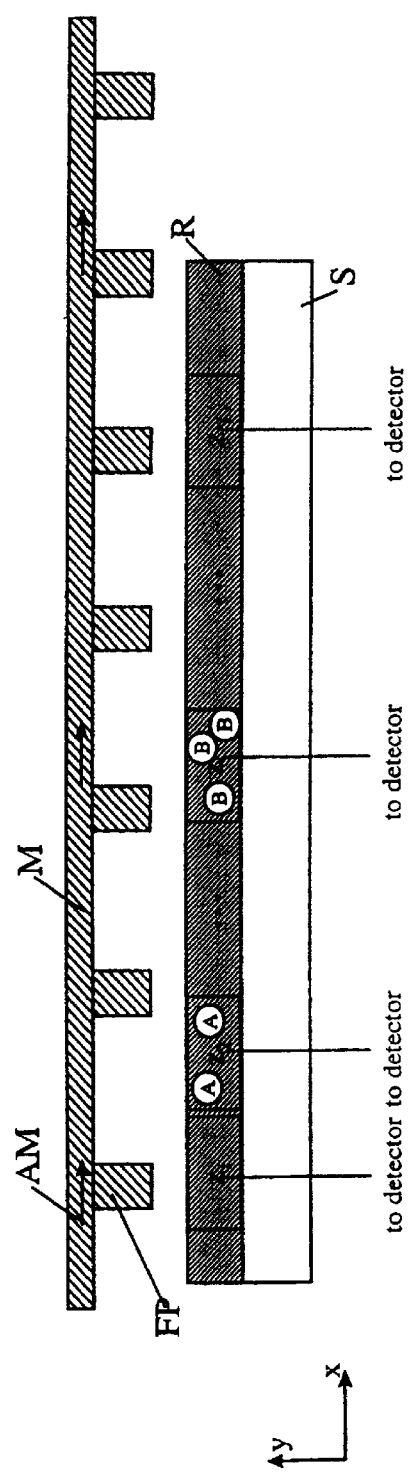
Fig. 19a
Fig. 19b

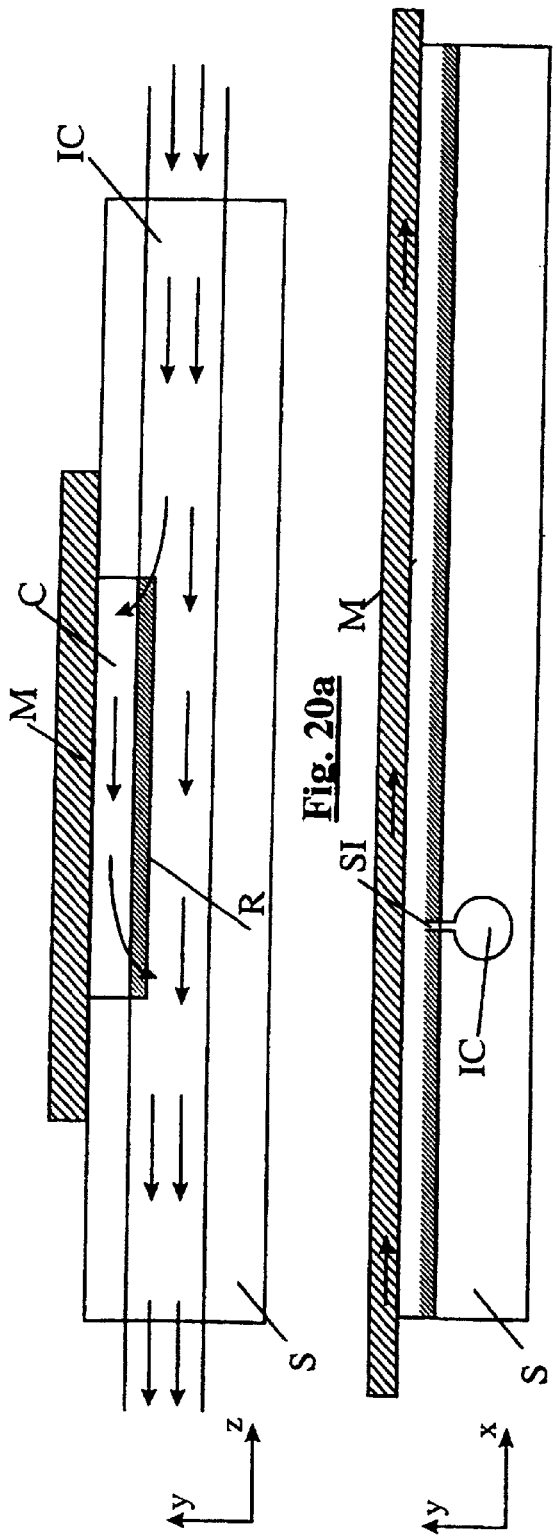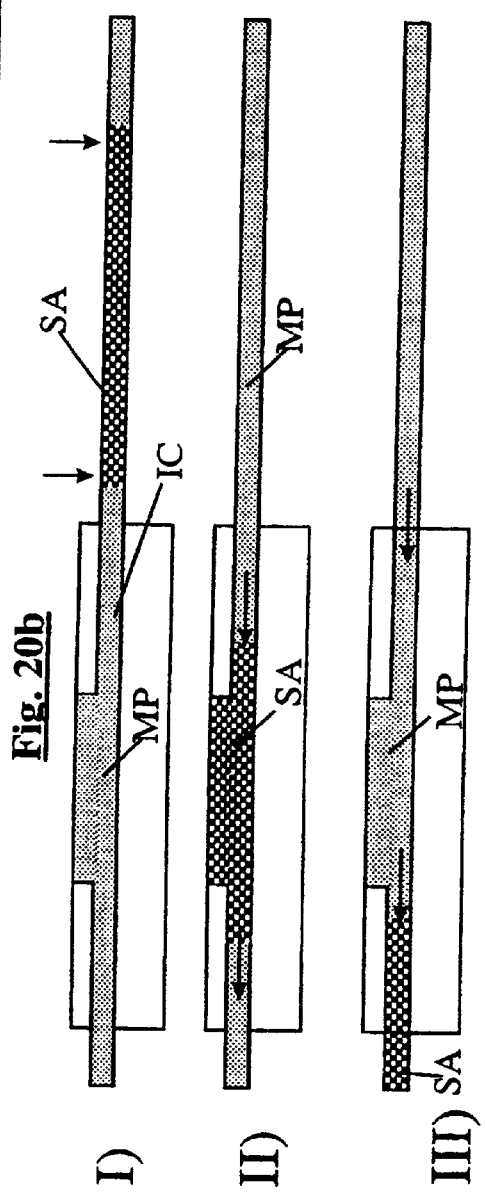
Fig. 20a
Fig. 20b
Fig. 20c

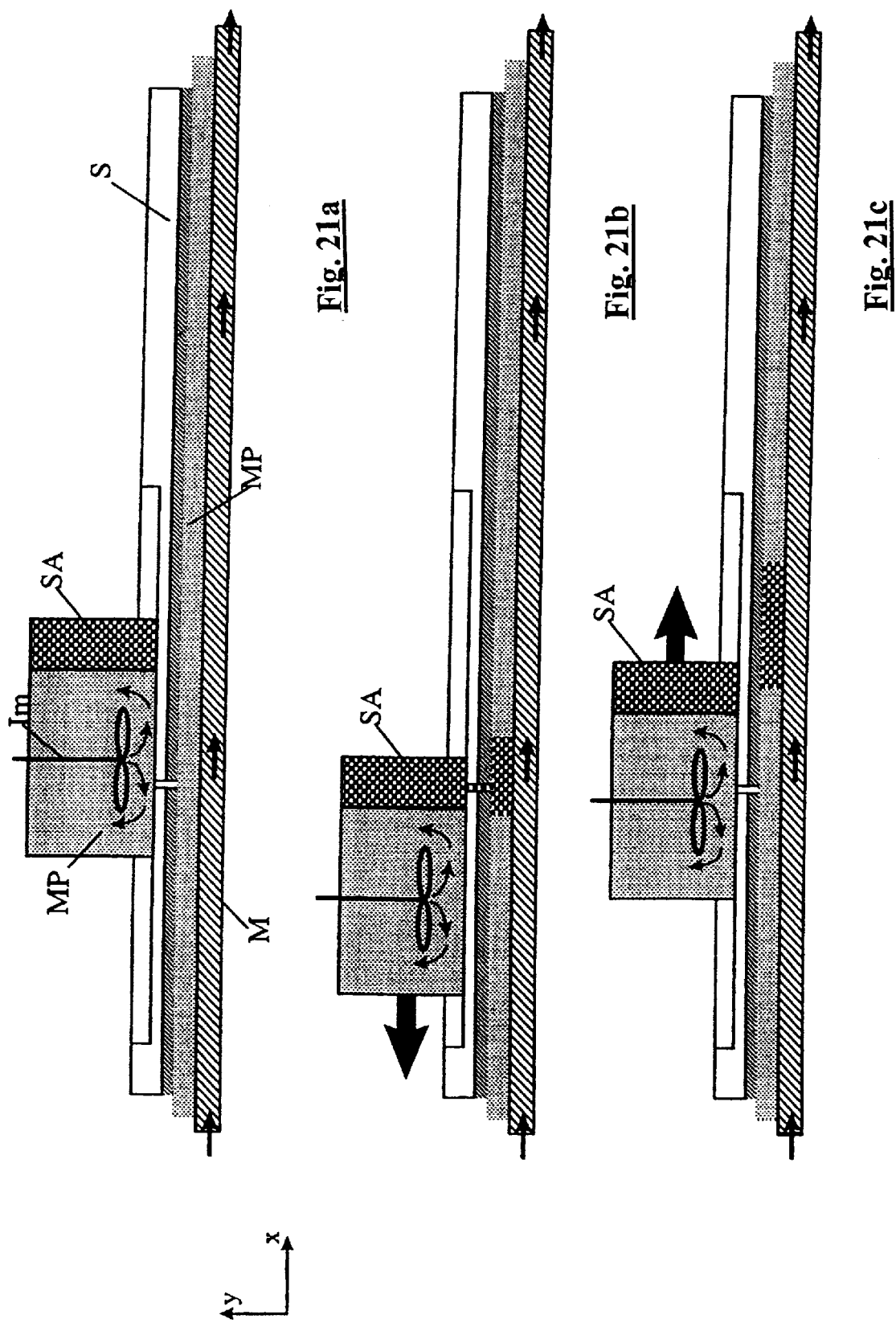

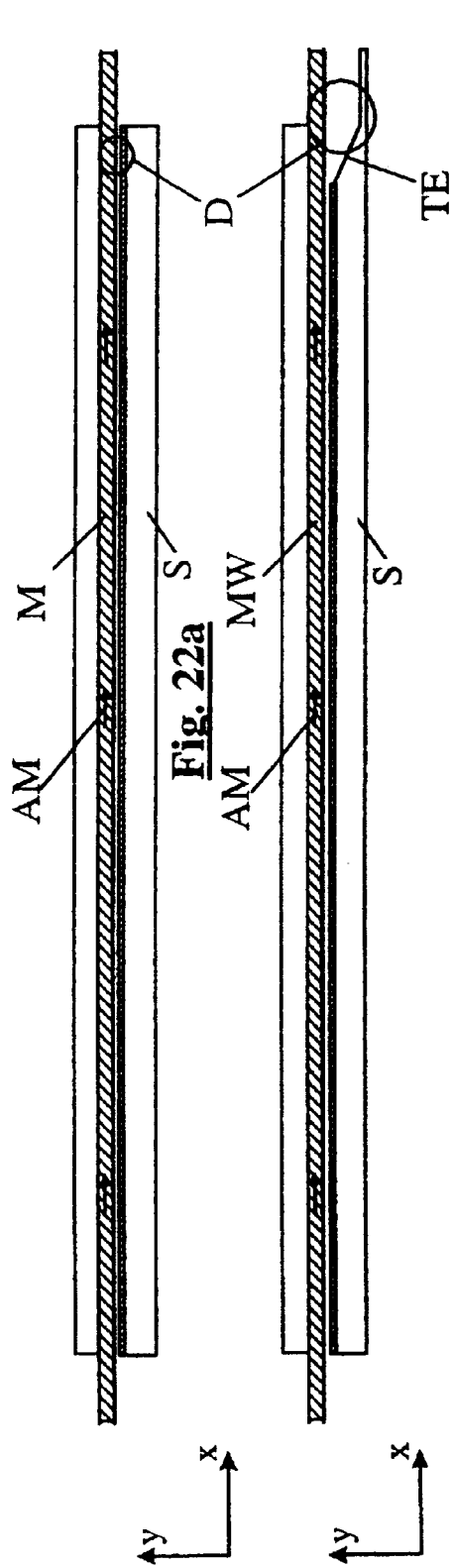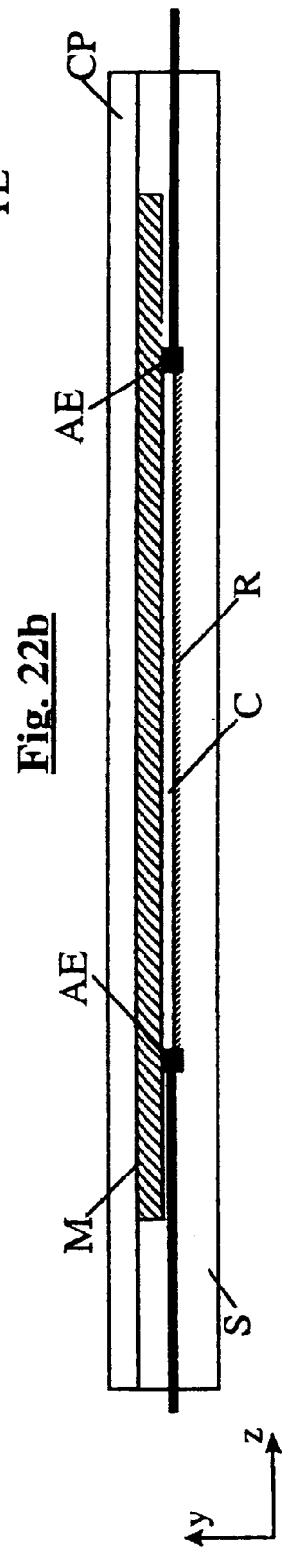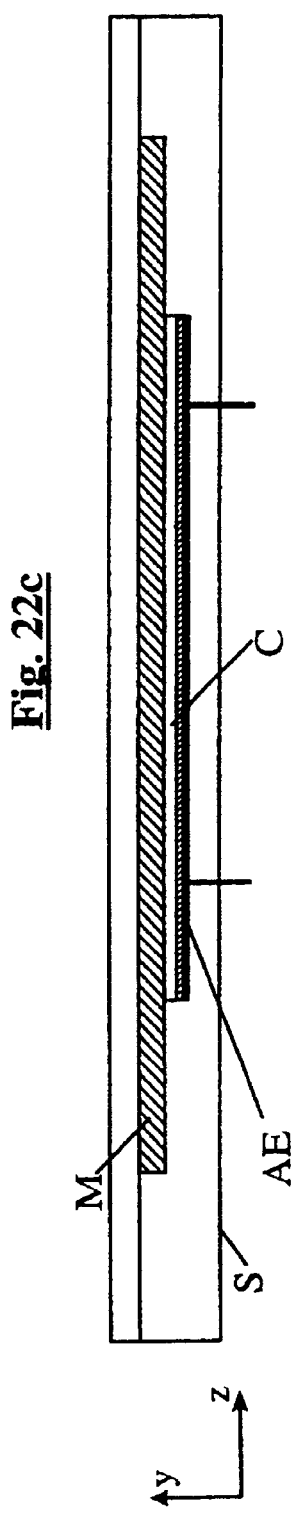

critical pair separation
$\alpha = 1.02$, $u_{opt} = 0.05$ m/s, $L = 1.2$ m
$k'_1 = 1./\alpha$, $k'_2 = 1$.

METHOD FOR SEPARATING A FLUID SUBSTANCE AND DEVICE THEREFOR

CROSS REFERENCE TO RELATED APPLICATIONS:

This is a U.S. National Phase Application under 35 U.S.C. §371 and applicant herewith claims the benefit of priority of PCT/EP98/03485, filed Jun. 3, 1998, which was published Under PCT Article 21(2) in English, which claims priority to European Application No. 97201699.2, filed Jun. 4, 1997, the entire contents of which are incorporated herein by reference.

FIELD OF THE INVENTION

The present invention relates to a new separation method and a device therefor. The invention is especially related to a method and a device for the separation of different components or species in a given sample for the purpose of their identification, wherein each different species has a specific and different residence time in a separation channel or is irreversibly retained at a specific and different position in said channel.

BACKGROUND OF THE INVENTION

In chromatographic chemical analysis methods, a sample containing one or more unknown components (sample species) is contacted with a carrier fluid (usually referred to as the mobile phase) which carries the sample solutes through a separation channel (or column) in which a retentive layer (usually referred to as the stationary phase) is arranged. During their motion through the separation channel, the sample species are continuously exchanged between the retentive layer and the mobile phase (the mobile phase is usually selected such that it has no or only a small affinity for the retentive phase). As the different sample species have a different affinity for the retentive layer, one species will spent more time in the retentive layer than another. As a consequence, all different species will move through the separation-channel with a different velocity. Arranging a detector device at the end of the separation channel, the different sample species will pass the detection point in a clearly separated mode. The response signal which is obtained when each ensemble of identical sample species passes the detector is commonly referred to as a peak.

To obtain an optimal performance, the width (i.e., in the time domain) of this peak should be as small as possible compared to the mean channel residence time of the given ensemble of sample species.

Presently, the two most popular chromatographic techniques are either pressure-driven or electrically driven. In pressure-driven chromatography, the mobile phase motion is generated by applying a pressure difference across the separation channel. The two most popular versions of pressure-driven chromatography are packed-column liquid chromatography (HPLC) and open-tubular gas chromatography (capillary GC), which are characterized in that different sample species have a different and unique residence time in the separation channel, and which are also characterized in that all sample species are detected only once. These two chromatographic techniques suffer from the fact that the pressure drop may not exceed a given value. As can be learned from Poiseuille's law, this pressure-drop limitation restricts the allowable column length and the applicable mobile phase velocity. Poiseuille's law also shows that the pressure drop limitation also puts a down limit on the effective column diameter d (open-tubular columns) or particle diameter $d_p$ (packed columns) which can be used when a given separation quality has to be achieved. The latter restriction puts a second down-limit on the analysis time, because the analysis time can be considered to be proportional to $d^2$ or $d_{p2}$. In electrically driven separations, a similar down-limit on the analysis time exists. In this case, the down-limit originates from the existence of a maximal allowable voltage drop.

The documents U.S. Pat. No. 4,874,507 and DE 41 08 820 describe continuous separation devices in which two oppositely moving surfaces are used to transport electrically charged or absorbed solid particles or fluid substances in two different directions. These devices and methods only enable to divide a liquid or solid feed stream into two different fractions. A complete single step fractionation is impossible, nor is it possible to characterize the nature of the different sample components from their unique and different residence time in the channel, as is possible with the methods known to those skilled in the art of HPLC or capillary GC.

In patent application EP 0 670 489 (Manz, 1997) a closed annular separating device is presented in which the use of a freely rotating internal toroidal ring is proposed as one of the possibilities to recirculate (i.e., without creating any net fluid displacement) the mobile phase in a closed channel.

The fact that a closed (annular) envelope is needed to cope with the pressure build-up inside the device restricts the field of application to batch mode separations (i.e., no inflow of fresh eluting mobile phase fluid during the actual separation). The device and method in EP 0 670 489 is hence not related to the type of once-through analytical separations known to those skilled in the art of HPLC or capillary GC. The device and method in EP 0 670 489 generates a complex system of continuously revolving and overtaking substance peaks, potentially causing undesirable competitive adsorption effects when two already separated substance peaks overtake each other. Furthermore, when the sample contains a large number of different species, inextricable chromatograms are obtained. In contrast thereto, it is a main objective of the present invention to provide a pressure-drop less operation of the type once-through analytical separation methods known to those skilled in the art of HPLC or capillary GC, characterized in that different sample species have a different and unique residence time in the separation channel, and which are also characterized in that all sample species are detected only once.

BRIEF DESCRIPTION OF THE INVENTION

In the method according to the present invention, the separation occurs in a separation channel, said channel being defined by at least two channel elements, and said channel being substantially sealed along its mantle surface, characterized in that the movement of the mobile phase in, through and out the separation channel is mainly caused by a relative axial movement of at least one of the channel elements compared to at least one of the other channel elements. In the present text, the notion "moving channel element" is used to refer either to a movable part of the channel wall or to a movable mechanical device positioned in the channel's interior.

In the device according to the invention the thickness of the channel is between 0.01 micron and 100 micron and preferably between 0.1 and 10 micron, and the width of the channel is between 0.1 micron and 10 centimeter and preferably between 10 and 1000 micron.

The methods according to the present invention are based upon the fact that, instead of applying a (pressure) force at the channel inlet only, the motion of the mobile phase fluid is generated by applying a force all along the column length. As a consequence, the mobile phase flow is generated without creating a pressure drop.

In the embodiments according to the present invention, the desired mobile phase flow is at least partly generated by the shear forces which originate from this moving element. In some of the embodiments according to the present invention, the mobile phase flow is furthermore sustained by one or more relief elements, such as one or more protrusions, recesses, holes or irregular porous-like structures, which are provided on the surface of the moving elements.

This implies that in all the embodiments according to the present invention, the mobile phase motion is generated without creating a pressure drop; and hence without the need to impose an excess pressure at the channel inlet, which pressure differences are considered as a basis for potential separation and identification problems. This explains why the moving channel element can also be apart of the channel wall, because, as the pressure inside the channel is substantially identical along its entire length, this pressure can be kept substantially equal to the pressure outside the channel such that the sealing of a channel mantle which consists of two independently movable wall elements poses no specific problem.

To obtain a suitable operation of the method and the device according to the present invention, any specific affinity between the surface of the moving channel elements determining the direction of the mobile phase flow and any of the mobile phase and sample fluid components should be excluded.

As will be shown below, the possibility to perform a chromatographic chemical analysis without creating a pressure drop offers a large number of advantages compared to the conventional pressure-driven chromatography. As already mentioned, the quality of the separation between two different sample species is maximal for a minimal ratio of the width of the eluted peaks to their residence time in the separation channel.

It can be learned from chromatographic theory that this ratio increases with the channel length. Considering now that the method according to the present invention puts no limit on the channel length, a first important advantage compared to the pressure-driven chromatography is noted.

Other advantages (e.g., larger efficiency per unit column length, faster separation times) originate from the fact that the method according to the present invention also allows to limit the following peak broadening phenomena typically encountered in chromatographic separations:

the finite time needed for the mass transfer in the mobile phase
i) the finite time needed for the mass transfer in the retentive phase the presence of lateral variations of the mobile phase velocity or of the ratio of mobile to retentive phase thickness when using channels with a large aspect ratio cross-section the molecular diffusion and longitudinal dispersion in the mobile phase
ii) the velocity gradient (s) in the mobile phase (y and z-direction).

As can be learned from chromatographic theory, the contribution of the phenomena i) and ii) to the peak broadening can be minimized by minimizing the channel diameter (open-tubular channels) or the particle diameter (packed channels). Whereas in pressure-driven chromatography a minimal channel or particle diameter is imposed via Poiseuille's law, the channel diameters which can be used according to the presently proposed method are only restricted by practical manufacturing and detection limits.

When considering columns with a circular or circular-like cross-section, the use of small (i.e., sub micron) diameter columns brings about major detection problems. Using mass flow sensitive detectors (such as e.g., a mass spectrometer), the detection suffers from the extremely small mass flow rates. Using on-column optical detection methods, the detection suffers from the extremely short optical path lengths. For these reasons, a preferred embodiment for the method according to the present invention involves the use of separation channels with a flat rectangular cross-section, allowing to combine the fast separation kinetics resulting from the small channel thickness with the large optical path length and flow rate resulting from the large column width. Preferentially, the thickness of the channel should be between 0.01 micron and 100 micron, and more specifically between 0.1 and 10 micron, and the width of the channel should preferentially be between 0.1 micron and 10 centimeter, more specifically between 10 micron and 1000 micron. As indicated under point iii) of the above list, the use of separation channels with a flat rectangular cross-section however might cause some undesired peak broadening effects. In the present text, a number of solutions (specially adapted manufacturing methods and/or the use of specific guiding means) is given to minimize the lateral variations of the mobile phase velocity or of the ratio of mobile to retentive phase thickness. An even more preferred proposed method is based upon the use of moving channel elements which allow to accommodate the entire mobile phase fluid into a plurality of compartments, said compartments being arranged such that the direct exchange of fluid elements between said compartments is substantially prevented.

One of the advantages of the use of such a compartmentalized embodiment is that the fluid near the side walls is not retarded with respect to the flow in the central portion of the channel. This implies that lateral variations (z-direction) of the mobile phase velocity are excluded. This is a feature which cannot be obtained with any presently existing chromatographic apparatus. Furthermore, the compartmentalized embodiment allows to add means which promote the mixing in the mobile phase such that the effect of lateral variations of the capacity ratio (i.e., the ratio of mobile to retentive phase thickness.) is eliminated by continuously redistributing the sample solutes in the lateral direction, while, due to the presence of the compartment barriers, these increased mixing rates do not cause any significant peak broadening. The possibility to limit the effect of the molecular diffusion and/or the longitudinal dispersion (see iv) to a single compartment is another feature which cannot be obtained with any presently existing chromatographic apparatus. Another advantage of a compartmentalized flow system can be found in the fact that in a shear-driven open-channel flow, variations in channel depth or channel width induce flow width induce flow mal-distributions, stagnant fluid layers and undesired velocity gradients. These effects may cause an unallowably large peak broadening. By organizing the flow into non-intermixing compartments, a fixed flow rate is obtained, independent of the variations in the cross-sectional dimensions. The manufacturing tolerances for a compartmentalized mobile phase flow are hence less stringent than for an open-channel shear flow. Another advantage of the compartmentalized flow is related to point v) of the above list, because all the fluid elements contained in a given compartment move trough the channel with the same net axial velocity such that there is substantially no net velocity gradient in the direction of the channel thickness (y-direction). The absence of such a velocity gradient is also a feature which cannot be obtained with any presently existing chromatographic apparatus.

In the methods according to the present invention, the channel may have any possible longitudinal shape, including straight, circular, spiral, helicoidal shapes. When having suitable thermal expansion characteristics, the channel elements can be made from any possible material (metal, semi-conductor, polymer, glass-like . . . ) or combinations of materials. If required, part of the surface of the elements can be coated with an inert, wear-free layer. To obtain a sufficient flexibility for the moving elements, segmented and/or laminated elements can be considered.

The devices according to the present invention can be operated at elevated temperatures and the column pressure (which is substantially identical at each point along the channel) can be put at any desired value (i.e., atmospheric and supra- and even sub-atmospheric). The device can hence be used to perform gas, liquid and super-critical fluid chromatography.

In a very attractive embodiment (the so-called Opposite-Moving-Channel-Elements device), the retentive phase is also subjected to a relative motion (opposite to the movement of the inert column parts) with respect to the detection point, while keeping the detection point fixed in space. In this way, the separation quality which can be achieved in a given column length can be drastically increased.

In the methods according to the present invention, the separation occurs basically in an open-tubular channel with freely accessible in- and outlet ports. This implies that the action of the moving channel elements can easily be combined with any other type of force field (electrical field, pressure force, gravitational, centrifugal force). This additional force field can for example be used to sustain the mobile phase flow, or to transport the fluid phase from the sample and mobile phase pre-treatment section to the separation channel and/or from the separation channel to the detection section, or even to create an additional separation effect.

BRIEF DESCRIPTION OF THE DRAWINGS

The invention shall be elucidated with reference to the figures and wherein is shown:

FIGS. 1. (a–d). longitudinal and cross-sectional views of possible embodiments and definition of reference frame (x,y,z-direction);

FIGS. 2. (a–c). schematic representation of the parallelism requirements;

FIGS. 3. (a–c). sagging and means to prevent sagging;

FIG. 4. method to obtain parallel running cover plate and channel substrate surfaces;

FIGS. 5. (a, b). schematic representation, of the side-bank concept;

FIGS. 6. (a, b). channel manufacturing by layer deposition and selective etching;

FIGS. 7. (a, b). channel manufacturing using a two-staged polishing tool;

FIGS. 11. (a–c). possible embodiments of the device according to the present invention;

FIGS. 14. (a–d). comparison between open-channel and compartmentalized flow;

FIGS. 15. (a, b). possible embodiments of a moving internal channel element carrying flow sustaining protrusions;

FIGS. 16. (a, b). possible embodiment for the application and the removal of the mobile phase and the sample liquid;

FIGS. 17. (a, b). possible embodiments for the arrangement of a micro-structured array in the retentive layer;

FIGS. 18. (a, b). increased mobile phase mass transfer due to the arrangement of protrusions on the moving and the stationary channel elements;

FIGS. 19. (a, b). separation by ad(b)sorption or reaction at a specific position or specific retentive layer zone;

FIGS. 20. (a–c). injection channel and preferred injection sequence;

FIGS. 21. (a–c). sample injection using the moving container concept;

FIGS. 22. (a–d). schematic view of possible on-column detection schemes;

DESCRIPTION OF PREFERRED EMBODIMENTS

Figure 8A:
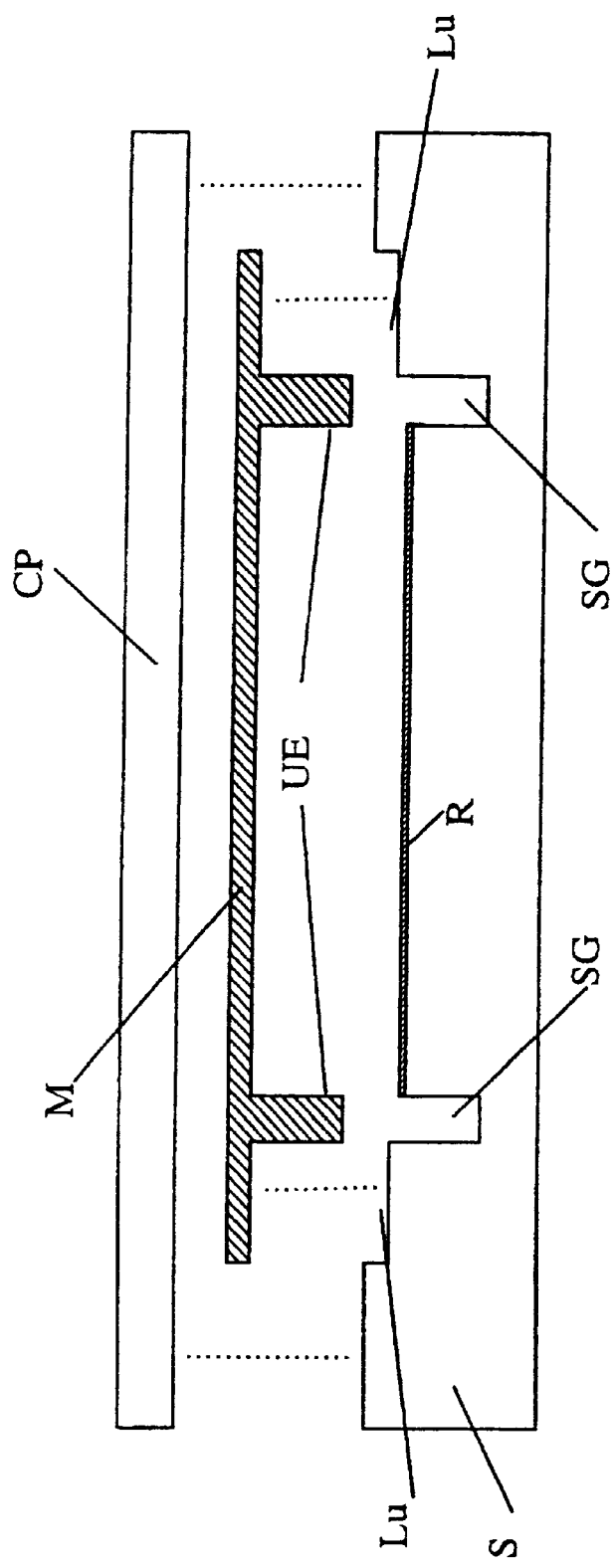
FIGS. 8. (a, b). moving wall element carrying so-called upstanding edges.
Figure 8B:
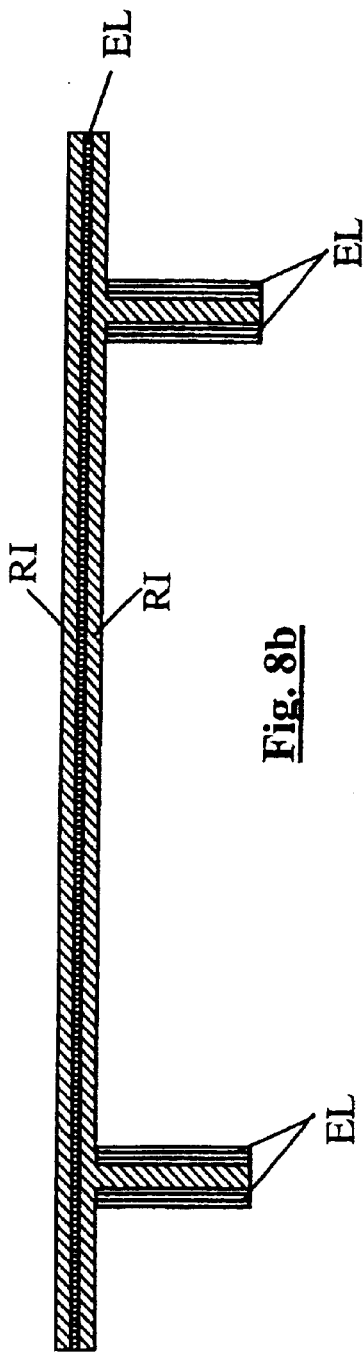
Figure 9B:
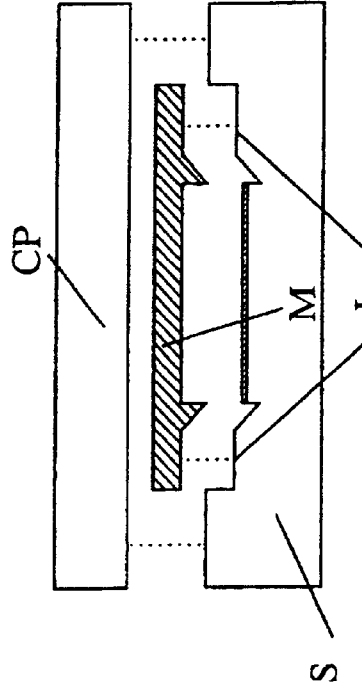
FIGS. 9. (a–d). some moving channel element embodiments.
Figure 9D:
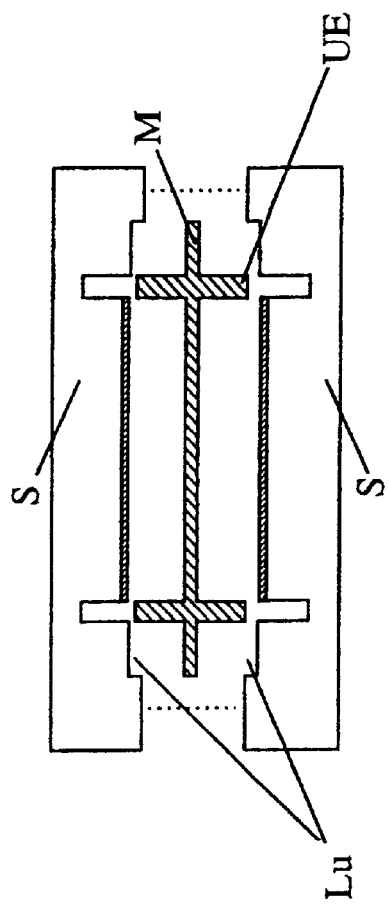
Figure 9A:
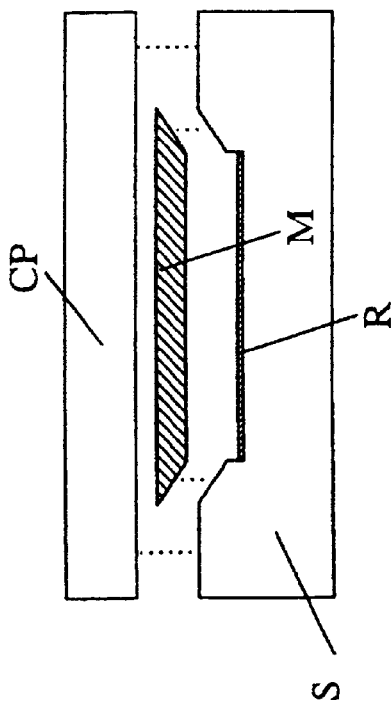
Figure 9C:
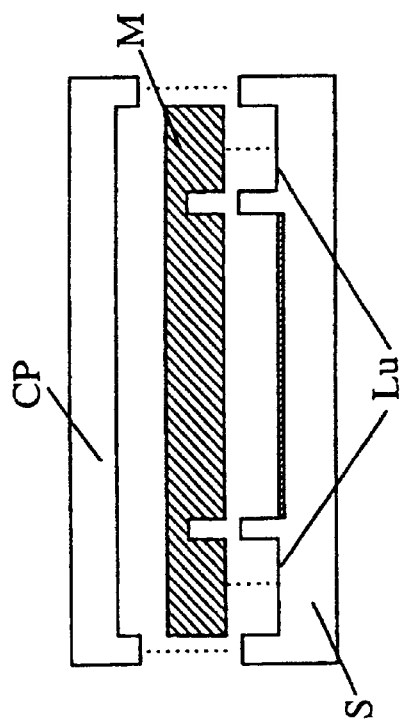

In the basic form of the separating device according to the present invention, the main movement of the mobile phase is completely or partly generated by axially moving two or more channel elements relative to each other. FIGS. 1 (a–d). presents a schematic view of the operating principle. The two basic variants for the "moving channel element" are given. In one variant, the movable element is part of the channel wall (FIG. 1a). In the other variant, the movable element is a movable mechanical device positioned in the channel's interior (FIG. 1b). In the presented embodiment, the movement of the movable channel elements is generated by an externally positioned motor device (MBD). Without having the intention to restrict ourselves to the presented designs, two typical arrangements for the cross-section of the channel (C) are given as well. one for the case of a moving wall element (FIG. 1c), and one for an internally positioned moving device (FIG. 1d). In the figures, the column parts which determine the direction of the mobile phase motion will be referred to as the moving column parts (M). The other column parts (which preferably have no or only a small relative movement with respect to the detection point) will be referred to as the stationary column parts (S). The direction of the movement of the moving channel elements and of the mobile phase fluid are respectively indicated by the arrows AM and AF. Preferably, the retentive phase (R) is exclusively arranged on the stationary column parts. To obtain the typical chromatograms, an injection device (I) is arranged near the channel inlet, and a detection device (D) is arranged near the channel outlet. In the preferred embodiments according to the present invention, a part of at least one of the moving channel elements is guided out of the active part of the separation channel such that the moving element can drag the mobile phase fluid (MP) out of the pre-column solvent vessel (SV1) into the separation channel, and out of the separation channel into the post-column solvent vessel (SV2). Using a moving wall element, a cover plate (CP) can be used to force the moving element against the stationary wall element in order to ensure the sealing of the channel along its entire mantle.

It should be noted that we do not which to restrict ourselves to the embodiments given in the figures accompanying the present document. It should be recalled that some parts of the embodiments presented in a given figure can be replaced by parts of embodiments presented in an another figure, or mentioned in the text, or by all other possible and suitable embodiments not literally mentioned in the present document, but having a similar functionality.

As already mentioned, when considering a channel cross-section with a large aspect ratio (i.e., one of the dimensions of the channel cross-section is much larger than the other dimension), it is critical to a suitable operation of the device that there is substantially no lateral variation in mobile phase fluid velocity, channel depth (d) and retentive layer thickness (δ). Therefore, at each axial position along the separating path, the best fitting line (FL1) running through the bottom surface of the retentive layer, the best fitting line (FL2) running through the top surface of the retentive layer, and the best fitting line (FL3) running through the top surface of the channel should substantially run parallel (FIG. 2a). Furthermore, the material points making up the different surfaces should all lie within a small margin around these fitting lines (condition of minimal roughness). Depending upon the required separation quality, this margin is typically of the order of one percent of the channel thickness. This implies that local imperfections on the wall surfaces or sagging of the moving channel element should be omitted. It should be noted that all fitting lines represented in FIG. 2a lie in the same cross-sectional plane, and although the parallelism has to be satisfied at each longitudinal position along the separating path, the absolute position (FIG. 2b) and the slope (FIG. 2c) of the best fitting lines may vary continuously with the axial position. Using moving wall elements which are sufficiently flexible in the longitudinal direction, the channel is allowed to follow the typical macro-waviness of commercially available polished silicon wafer surfaces (FIG. 2b). Apart from being flexible in the longitudinal direction, the moving wall elements should be sufficiently rigid in the transversal direction such that sagging across the channel is prevented (FIG. 3a). This rigidity can be controlled by selecting appropriate materials and an appropriate thickness. To combine longitudinal flexibility with a transversal rigidity, all conceivable types of laminated or segmented tapes or strips can be considered. A laminated moving element preferentially consists of a thin flexible layer (preferentially between 1 and 100 nm) of a material with a suitably polished surface and suitable sliding characteristics, followed-by a thicker elastic layer serving as a support for the thin layer and allowing to account for the manufacturing tolerances of the different channel elements, and followed by a wear-resistant layer which will be in contact with the cover plate.

When the moving element is too flexible in the lateral direction, the moving element can be tensioned by arranging tensioning means (TM) along both sides of the element (FIG. 3b). These tensioning means can then be guided through a rail-like system (RA) arranged alongside the channel (FIG. 3c). Preferentially, this rail system is arranged within the cover-plate. If required, means can be added to control the tension which is applied to the moving channel element:

Using an internally positioned moving channel element, pre- and post-column mechanical guiding and tensioning devices can be provided to control the position of the moving mechanical device from outside the separation channel.

To minimize the stresses in the moving channel elements, a possible approach would be to use a cover plate which is the negative replicate of the original substrate surface on which the separation channel is arranged. In this way, the channel bottom wall and the cover plate can be positioned such that they have a substantially matching and parallel running macro-scale waviness (FIG. 4). Preferentially, the contact surface between the cover plate and the moving element is minimized (see for example the recess in the cover plate in FIG. 3c).

The moving channel elements may have any desired thickness, but should preferably be between 1 nanometer and 5 millimeter. The moving channel elements may be impermeable, semi-impermeable or permeable. A permeable or semi-impermeable channel element can be used to facilitate the wetting of the moving element prior to entering the channel, because the permeable material allows to generate a flow perpendicular to and through the element, e.g. by applying an under-pressure at the back-side of the moving channel element (see PU1 in FIG. 16a). In the channel, the sealing of the pores of the permeable moving wall element is easily ensured by its contact with the impermeable cover plate wall. Preferentially, this cover plate is arranged with an elastic sealing layer. Using an elastic moving channel element (e.g., using a polymer such as PDMS), the channel element can also be made permeable by arranging a large number of micro-slits (preferentially with rectangular cross-section) into the material. Using very narrow slits, these slits are normally closed by the elastic properties of the material, but they can be opened by applying a given stress to the material. Applying this stress only near the channel inlet or near the injection point, these slits can be temporarily opened, allowing to enhance the wetting of the channel element. Once in the channel, the slits can be closed again.

One way to achieve the parallelism requirements given in FIG. 2 (a–c). is to use a moving channel element which is substantially flat (i.e., in the z-direction) and smooth and pressing this element against so-called side-banks (SE) arranged alongside of the separating path (FIGS. 5a, b). These side-banks are preferentially machined with at least the same degree of flatness and smoothness as the channel bottom wall and run substantially parallel with it (even when this bottom wall is curved). The width of these side-banks should preferably be between 10 to 300% of the channel width (W). Considering a preferred class of channel widths, the total zone over which a high degree of flatness and smoothness has to be achieved should hence preferably extend over a distance between 100 and 3000 micron. By removing the top layer of the surface parts (Sx) aside of the side banks, it can easily be understood that these parts require no specific surface finish. After the column parts have been joined, the side-banks serve to support the moving wall element and maintain the moving element in a substantially fixed and uniform distance from the channel bottom wall. During the normal operation (FIG. 5b), the moving element (M) is preferentially pushed against the side-banks by means of a cover plate (CP). Preferentially, this pushing force can be regulated using regulating means (Re). Preferentially, a thin, wear-resistant and low-friction coating layer (Co) is applied on the side-banks and/or on the moving element. In literature, sufficient methods are described which allow to apply such a layer with a nanometric accuracy. The wear and friction can further be reduced by using textured coating layers. If desired, additional means can be added to improve the sealing. These means may involve the use of an "active sealing", using electromagnetic, electrostatic or any other suitable means. When multiple moving wall elements are present, a separate cover plate can be used for each of them.

To avoid an ineffective operation of the device due to the presence of undesired species (e.g., dust, moisture, . . . ) on the surface of the channel elements, the device can be equipped with means to eliminate these undesired species from the channel elements prior to the joining of these members. These means can be either electrical, electrostatic, electromagnetic, mechanical, or of any other suitable nature. Heating means can be considered as well. Arrangements can also be made to pre wet the channel with the mobile phase fluid before the moving wall is put into functioning or before the channel elements are joined.

To avoid the existence of undesirable secondary flows and/or stagnant fluid zones (which both have a peak broadening effect), the nominal channel depth value, i.e., defined as the mean difference between the portions of FL3 and FL2 which are situated within the channel width, should also be substantially identical at each point along the channels' longitudinal axis. For the same reason, it is also desired that the mean cross-sectional width (i.e., averaged over the y-direction) is substantially identical at each point of the channels' longitudinal axis.

One possible way to manufacture separation channels with the desired parallelism and the desired uniformity of the cross-sectional dimensions would be to start from a highly polished substrate (SU) which is locally sufficiently flat over a predefined zone with a width preferentially between 100 and 3000 micron (longitudinal macro-scale waviness is allowed), then deposit a layer of substantially uniform thickness and then recessing the channel in the deposited layer while leaving the surface parts needed to form the side-banks unaffected (FIGS. 6a, b) For this purpose, one can rely on all techniques for layer deposition, mask making and selective etching known to those skilled in of the micro-electronics manufacturing. These methods presently allow to achieve a lateral accuracy of the order of 0.1 micron or less and a depth accuracy of the order of a few nanometer. To obtain a substantially uniform etch depth, the interface between the substrate and the deposited layer can be used as an etch stop, or a specific etch stop layer can be used. As depicted in FIG. 6 (a, b), several other layers (e.g., a wear-resistant coating Co) can be deposited together with the layer (SB1) needed to form the side-banks. Using a sacrificial inter-layer (S1), it is even possible to add a suitable retentive layer during the same process (FIG. 6b). Other combinations of layers and deposition sequences are of course conceivable.

The channel can also be manufactured by means of direct wheel grinding or diamond point turning. In a specifically adapted technique, the channel is recessed using conventional polishing or grinding techniques but using a polishing or grinding tool with a micro-machined, two-staged head (PH) which has one of its dimensions matching the desired channel and side-bank width (FIGS. 7a, b) Moving the polishing tool back and forth along a predefined path along the substrate surface, the same polishing tool can be used to simultaneously polish the channel and the side-bank, thus guaranteeing a maximal parallelism between the side-banks and the channel bottom wall and a maximal-uniformity of the channel depth and width along the entire channel length. The method can be applied on flat as well as on non-flat surfaces. Using a circular polishing tool, the tool can be rotated during the polishing operation. If desired, grooves (Gr) can be arranged alongside the channel path to remove the polishing liquid. After the manufacturing process, these grooves can for example be used to accommodate the upstanding parts which can be arranged on the moving channel elements (cfr FIGS. 8a, b).

Adapting the moving channel element(s) with so-called upstanding edges (UE, see FIG. 8a), it is possible to ensure the sealing of the separation channel without posing any additional requirements on the construction tolerances of the side plates: using the elastic properties of the upstanding edges, the sealing occurs by forcing the upstanding edges to move in the side-grooves (SG) which are arranged just aside of the retentive layer (R). Preferentially, the moving element consists of a number of elastic (EL) and rigid (RI) elements. In the figure, the zones (Lu) are indicated where a lubrication liquid can be applied which cannot mix with the mobile phase. Examples of other types of specifically adapted moving channel elements are given in FIG. 9. (a–d)

Figure 10A:
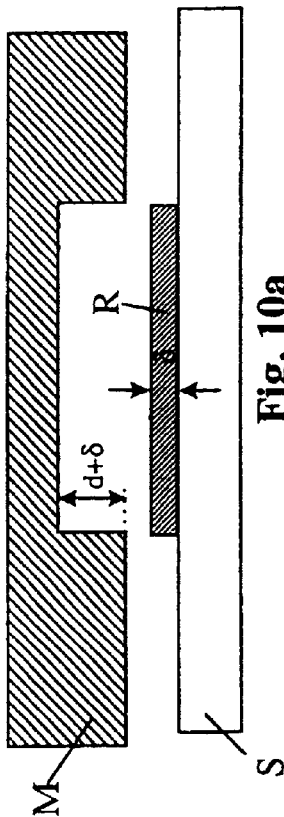
FIGS. 10. (a–f). some possible embodiments in which part of the channel is recessed in the moving channel element.
Figure 10B:
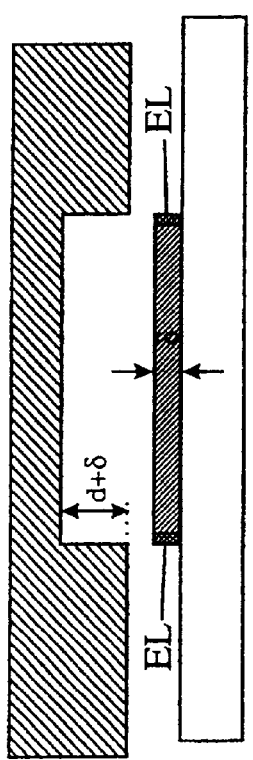
Figure 10C:
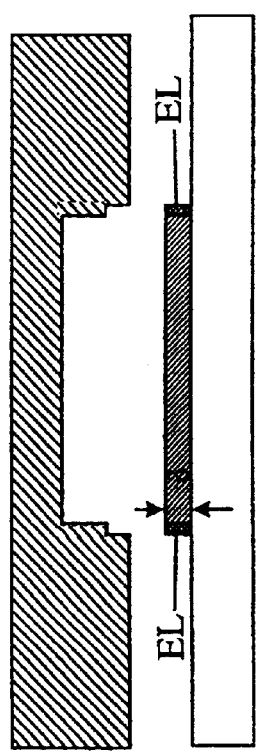
Figure 10D:
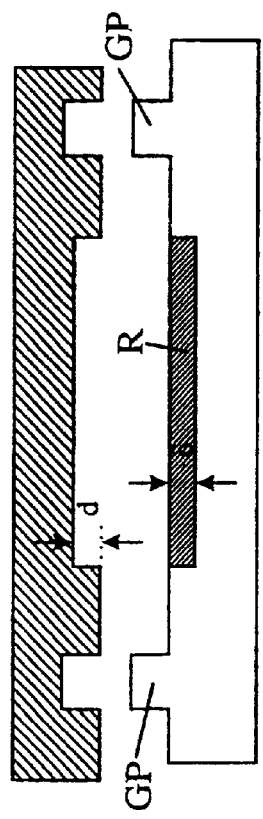
Figure 10E:
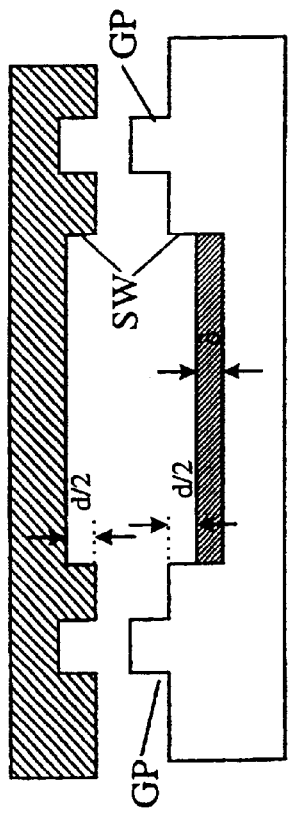
Figure 10F:
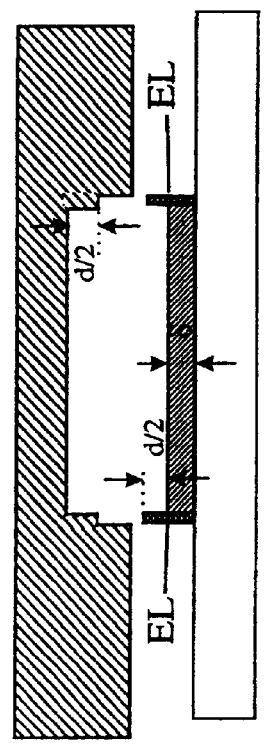

In some of the embodiments according to the present invention, the space required to accommodate the mobile and the retentive phase is partly or completely recessed in the moving element (FIG. 10a–f). When the channel is fully recessed in the moving wall, the retentive layer simply has to be applied on a locally flat surface (FIG. 10a). The sealing can be improved by adding a thin elastic layer just aside of the retentive layer (FIG. 10b–c). In another variant, the portion of the channel in which the retentive layer has to be arranged is arranged in the stationary wall and the remaining channel portion is recessed in the moving wall (FIG. 10d). In this case, the top surface of the retentive layer lies in the same plane as the surface of the substrate in which the recession has been made. The relative position of the stationary and the moving wall is then directed by means of a guiding peg system (GP), preferentially extending along the entire separation path length. In a theoretically preferred variant, one half of the sidewalls (SW) moves with the non-retentive wall, while the other half is connected to the retentive wall (FIG. 10e–15b). Neglecting the effect of manufacturing tolerances, the radially averaged velocity (i.e., in the y-direction) in this variant is exactly equal to one half of the moving wall velocity at each point of the lateral direction, even in the vicinity of the side walls. When performing a chromatographic separation in a flat rectangular flow system, the absence of a velocity gradient in the lateral direction is a highly desired characteristic to avoid peak broadening effects. The absence of a lateral gradient (i.e., in the z-direction) of the radially averaged mobile phase velocity is a feature which cannot be obtained with any pressure-driven flow.

In some embodiments according to the present invention, the moving channel elements are pushed or pulled through the channel by a motor device and a suitable transmission means (see FIG. 1 (a–d). In these embodiments, the use of a sufficiently flexible moving channel element allows the channel to be arranged on any type of flat or non-flat rigid surface (such as cylinders, cones, . . . . ). Manufacturing the other channel elements (stationary channel elements and cover plates) also from a sufficiently flexible material, and by limiting the total column thickness (t) preferentially to a few millimeter, the column can be wound several times around a given mechanical object. This allows to arrange long column lengths (up to 100 m and more) in a relatively small volume. In a preferred variant, the moving element is arranged as an endless moving belt-like device (FIG. 11a).

In the other embodiments, the moving channel element is linked to a suitable moving surface, such as a translating plate, a rotating flat surface (FIG. 11b) or a rotating cylindrical or conical surface (FIG. 11c). The stationary channel elements are then preferably arranged on a matching surface. In the basic embodiments according to the present invention, the channels which are arranged on these surfaces are preferentially straight or circular. To obtain very long channel lengths on a small surface, channels with a spiral (on flat disks) or helicoidal (on a cylinder or a cone) longitudinal shape can be considered as well. Care has to be taken that the sealing between the different rigid channel elements is not disturbed by the macro-scale waviness of these elements. If this would be a problem, it can be circumvented by covering at least one of the rigid moving surfaces with an elastic buffer layer and a thin (possibly segmented) layer of a material with sufficient longitudinal flexibility.

In the embodiments in which the moving channel element (s) continuously re-enter the separation channel, as is for example the case for all the embodiments presented in FIG. 11 (a–c), a cleaning and/or diluting device (CL) should be provided which allows to remove, deactivate and/or dilute the sample solute species after their passage at the detection point. In this way, the sample species are prevented from re-entering the channel such that they only make one single (detectable) passage at the detection point. These means may include suctioning, scraping, evaporating, heating or brushing devices suited to remove the species from the moving channel elements, and jet and impeller devices to dilute the outlet flow with pure mobile phase liquid. When the sample species have some special property or functional part without which they cannot be detected, arrangements can be made to deactivate this property or functional part. When a circular or annular or any other normally closed channel is used, part of the circle or of the annulus should be left open such that a cleaning device can be positioned between the injection and detection point.

The retentive layer can for example be obtained by depositing a porous material layer using conventional CVD techniques. Another possibility arises from the techniques which presently allow to deposit polymer layers with a mono-layer accuracy. Another possibility consists of selectively producing a porous layer using selective ion beam milling and etching techniques.

In a preferred embodiment, the retentive layer consists of a high density array of substantially parallel pores, yielding fast stationary mass transfer kinetics because of the minimal tortuosity. Such an array can be obtained via present state-of-the-art micro- or nano-imprinting techniques.

The optimal accessibility of the channel surface during the manufacturing procedure also allows to apply a retentive layer which at least partly displays a gradual or discrete variation of the chemical and/or physical characteristics of the material of which it is composed. This is an especially preferred variant because it allows to perform the equivalent of a so-called multi-effect separation in a single channel. Conventionally, such multi-effect separations have to be performed by feeding the outlet of a column with a given stationary phase to the inlet of a second column coated with another stationary phase.

A porous layer, or a layer with specific adsorptive, absorptive or reactive properties can also be arranged on at least one of the moving wall elements. This layer can for example be used to facilitate the wetting (with the mobile phase liquid) of the moving channel element or to prevent a given component from entering the retentive layer by irreversibly removing this component from the mobile phase. Using a retentive layer consisting of a multitude of different zones, such an ad(b)sorbing moving wall can be used to transport a given collection of sample species past a given zone towards a following zone without spending any substantial time in the retentive phase of said first zone.

Means for heating the mobile phase fluid can easily be integrated in the stationary wall elements and can even be incorporated directly within the retentive layer. These means can for example be electrical resistors or micro-machined channels containing a suitable heat transfer fluid. Using an electrically conductive material, the heating means can be the channel element itself. Using such heat transfer means and considering a flat rectangular shape for the channel's cross-section, which is due to its maximal surface to volume ratio a the most preferred shape for heat transfer purposes, it is obvious that the devices according to the present invention allow for a very effective heat transfer. This can be exploited to reduce the time needed for column heating and cooling between two successive analysis, hence saving column downtime, and to increase the rate with which temperature programmed separations can be performed. Applying a plurality of heating and cooling means, the excellent heat transfer characteristics can also be exploited to selectively impose different temperatures at different longitudinal positions of the column. If required, heating means can also be accommodated in a moving wall element. Apart from temperature programmed separations, the device according to the present invention also allows to vary the composition of the mobile phase liquid in the pre-column vessel allowing to perform so-called gradient elution separations.

A large scale production of the required channel elements can for example be obtained using replication methods presently used in the replication of microelectronics and of magnetic, optical and opto-electronic nanodevices. These replication methods include the processes of molding, imprinting, embossing, metal plating, electroforming, molding.

Considering this replication possibility, it is important too note that,the channel manufacturing methods discussed in FIGS. 5a, b and 6a, b an equally well be used to machine a negative mold for the channel element, which can then be used in a subsequent replication step to obtain a positive image of the required channel element.

One of the possibilities to manufacture long channels (i.e., longer than possible with fully rigid substrates such as wafers) would be to imprint the required channel shape in a thermoplastic layer arranged on top of a continuous strip or belt, using continuous embossing roller replication techniques well known to those practicing the art. Using this technique to obtain a continuous channel strip, a channel mold (either a positive or a negative image) has to be arranged on the embossing roller in such a way that the shape of the channel extends in a seamless way along the entire circumference of the cylindrical mantle of the roller. Such a mold can be manufactured using the same techniques as those used for arranging the channel shape on a flat rigid substrate (polishing of cylindrical surfaces is sufficiently described in literature and the cylindrical nature of the surface poses no specific additional problem for the layer deposition and etching steps). If desired, the mold can be arranged such that desired protrusions or recesses (e.g., to from the upstanding edges presented in FIGS. 8a,b or the guiding pegs presented in FIGS. 10a–f) can be arranged during the same production step.

This procedure can either be used to directly obtain a plastic replicate of the desired channel (using a negative image mold), or to obtain a negative plastic replicate of the channel (positive image mold) which can then be treated in a subsequent step by any suitable continuous layer deposition method to obtain a positive replicate of the channel in a metal or semi-conductor material. Using a highly polished, un-profiled embossing roller, the same embossing method can be used to obtain continuous strips of fully smooth and flat moving wall elements. If required, laminated versions of the moving wall can be obtained in additional manufacturing steps, prior to or after the embossing step.

The presently existing micro- and nanostructure manufacturing and replication techniques also allow to arrange one or more specifically purposed protrusions or recesses on the channel elements. The envisioned protrusions or recesses may be either rigid or flexible or may exhibit a combination of both types of material behavior. The protrusions or the recesses may be cylinders, semi-spheres, triangular, all types of polygonic rods, crosses, or any other type of mechanical objects. Protrusions or recesses having profiled surfaces can be considered as well as protrusions having fully flat and smooth surfaces. The protrusions or recesses may either extend over the entire channel width or only over part of it. In a specific variant, all or part of the protrusions or recesses are mechanically linked to so called upstanding edges delimiting the lateral extend of the separating channel. Apart from recesses or protrusions, the arrangement of one or more holes in the channel elements can also be considered. In the remainder of the text, we will focus upon the functionality of the surface structures which protrude from the channel elements, even when these are the result of arranging so called relief elements such as recesses or holes on the channel element. Therefore, at each instance where the word "protrusions" is used, it should be kept in mind that these protrusions may also be the result of arranging a recess or a hole in the channel element. It should be noted that said relief elements can also be arranged in the form of an irregular porous-like structure.

Figure 12A:
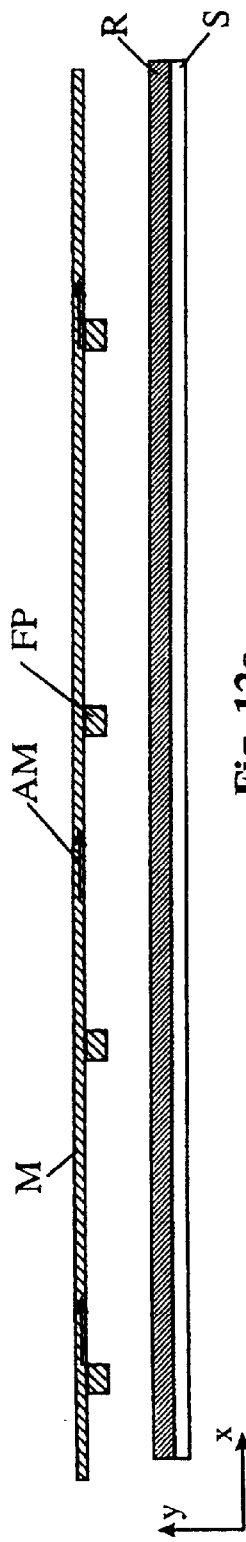
FIGS. 12. (a–d). possible embodiments of a moving channel element carrying flow sustaining protrusions.
Figure 12B:
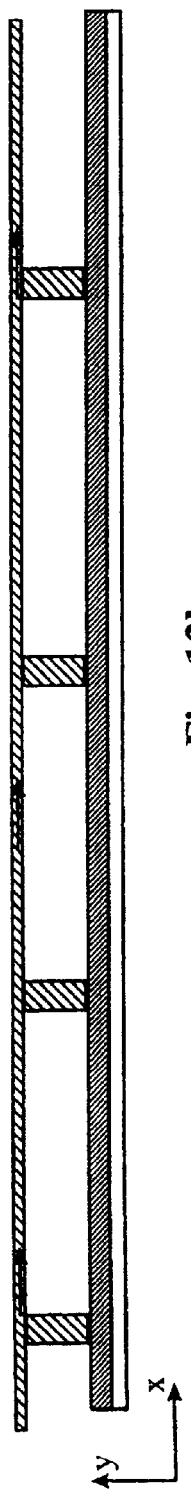
Figure 12C:
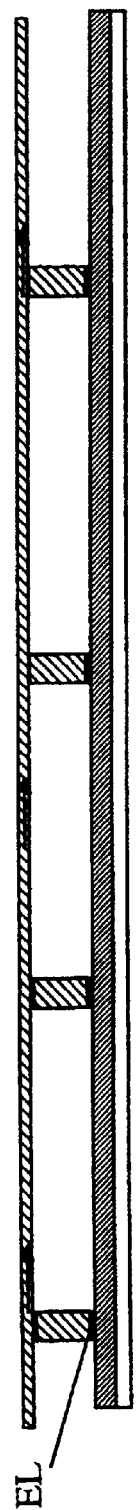
Figure 12D:
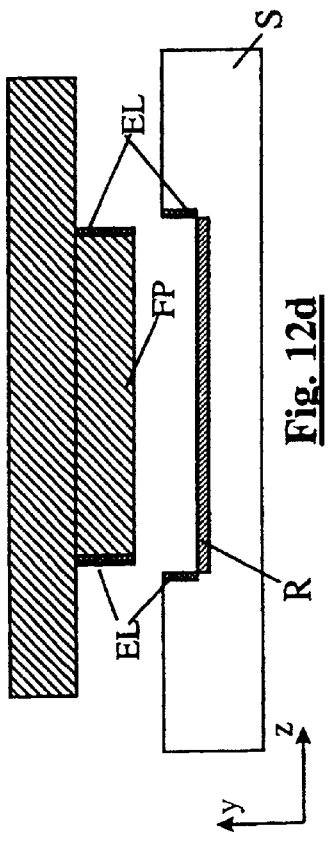

The envisioned protrusions can for example be used as a means to sustain the mobile phase flow (FIG. 12a). Protrusions (FP) which are specifically added with this purpose will be further referred to as "flow sustaining protrusions". A special case is obtained when these flow sustaining protrusions substantially extend across the entire channel depth such that they substantially touch the retentive layer (FIG. 12b). If desired, an elastic sealing layer (EL) can be applied at the end-face of the protrusions in order to obtain a perfect sealing between these protrusions and the retentive layer (see FIG. 12c). If desired, an elastic sealing layer (EL) can also be applied along the channel side-walls and/or along the side walls of the protrusions (FIG. 12d, cross-sectional view). The protrusions may of course also be fully elastic. Considering the above arrangements, it is obvious that it is possible to obtain a moving wall structure which is divided into a number of preferentially perfectly sealed compartments. Such a structure allows to transport the mobile phase fluid through the separating channel without any substantial inter-mixing of the mobile phase liquid between the different compartments.

Figure 13A:
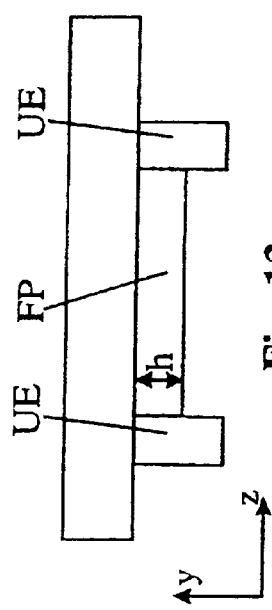
FIGS. 13. (a–c). possible embodiments of a moving channel element carrying flow sustaining protrusions.
Figure 13B:
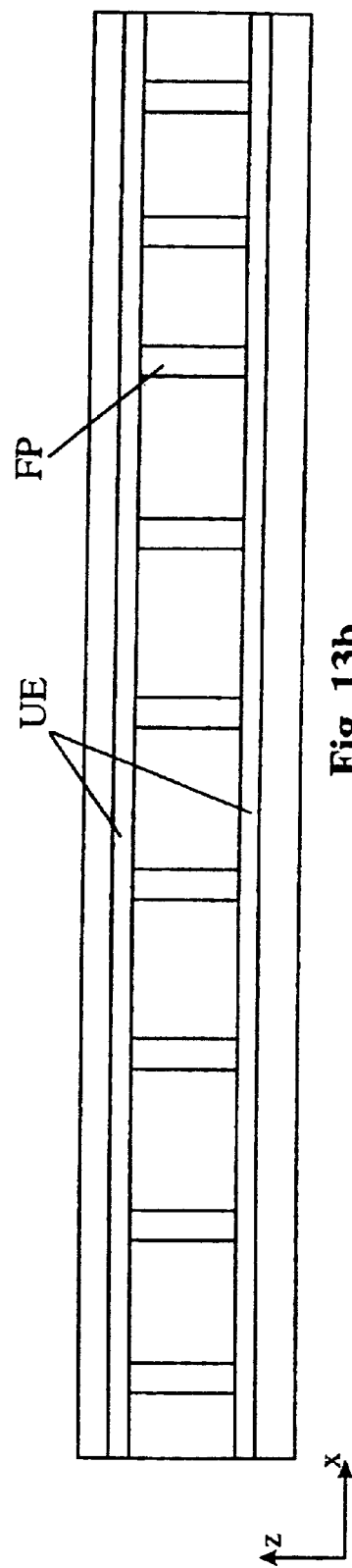
Figure 13C:
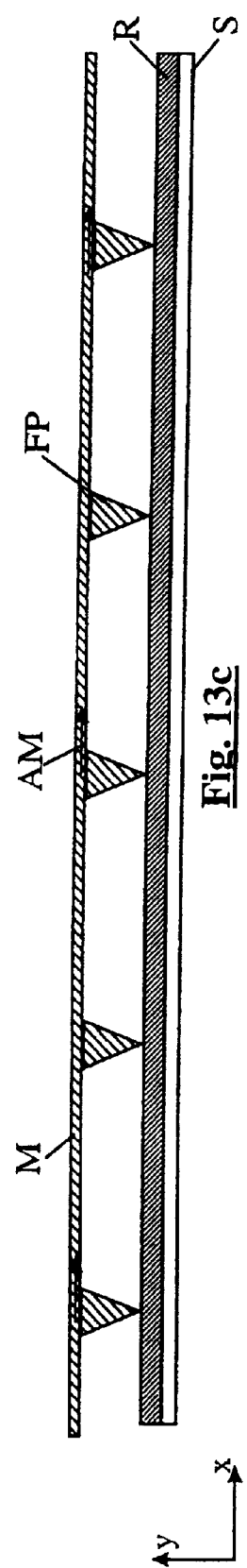

A similar array of non-intermixing compartments is obtained when protrusions having a height (h) which is equal to the desired channel depth are arranged such that they form an integral part with two so-called upstanding edges delimiting the lateral extend of the separating channel (FIG. 13a, b). Preferentially, the distance over which the upstanding edges protrude from the surface of the channel element is at least equal to the height (h) of the flow sustaining protrusions. The wear of the protrusions sliding past the retentive layer can be minimized by considering triangular shapes such as shown in FIG. 13c.

Although not preferred for reasons of mechanical strength, a compartmentalized fluid transport system can also be obtained by arranging micro-scaled rectangular slits into an internally positioned moving elastic strip or tape.

The above described compartmentalized embodiments are especially preferred, because they allow to transport the entire mobile phase through the separation channel without any, substantial direct longitudinal mixing between the compartments. Preferably, the compartments are arranged in a micro-structured array wherein each compartment has a longitudinal width between 0.1 and 10 micron. When the sealing is perfect, the only way by which sample species (SA) can move from one compartment to another is by passing via the retentive layer. This is an especially desired characteristic because it allows to drastically reduce the peak broadening effects originating from the mobile phase molecular diffusion (FIG. 14a) and from the mobile phase velocity gradient(s) (FIG. 14b), because the compartment barriers substantially limit these effects to the width of a single compartment unit. This is a feature which cannot be obtained with any presently existing chromatographic apparatus.

Considering the equivalence between the flow in the compartments with cavity flow, depending upon the distance between the protrusions, a more or less significant secondary flow (Sf, FIG. 14a, d) can be obtained in each of the compartments. This might yield another advantage because this secondary flow increases the mobile phase mass transfer rate compared to the pure unidirectional flow encountered in conventional open channel flow systems, while its undesired longitudinal mixing effect remains limited to a single compartment.

It should be noted that said compartments can also be arranged in the form of an irregular porous-like structure. In this embodiment the lateral mixing is however strongly inhibited.

Preferentially, the materials for the compartments can be selected such that the compartments are sufficiently flexible to adapt to the undesired waviness and roughness of the retentive layer and the other surfaces past which the compartmentalized element is moved. Without having the intention to restrict ourselves to any specific material, a suitable candidate to make such a compartmentalized moving element would be PDMS. If required, a thin coating layer can be added to exclude any affinity between the moving element and the sample and mobile phase components.

Flexible compartments can also be used in combination with a regular array of micro-structures arranged on or more of the other channel elements to induce a lateral mixing inside the compartments by continuously deforming the compartments in a regular and pre-defined manner. An increased lateral mixing is especially preferred because it allows to eliminate the peak broadening effects caused by lateral variations in the ratio of mobile to retentive phase thickness. Mixing can for example also be enhanced by working at an elevated temperature or by working under sub-atmospheric conditions, or by including ultra-sound or electrical means. The latter means can be used to induce an electrically driven secondary flow between the two channel side-walls. Mixing can also be achieved by inducing vibrations in ore more membranes or wires arranged inside the interior of the compartments. Mixing can also be promoted by adding inert sub-micron particles to the mobile phase fluid. The use of micro-machined mechanical mixing devices incorporated within the compartments can be considered as well.

Flow sustaining protrusions extending over the entire channel depth can also be used to ensure a fixed and uniform distance between the moving element and the retentive layer. This concept can be used for wall elements as well as for internal channel elements and can be used in combination with channels having all possible cross-sectional shapes, including circular (FIG. 15a, b), semi-circular, ellipsoidal, square and rectangular shapes.

Using flow sustaining protrusions, it might be necessary to include means to fully wet the moving wall with mobile phase fluid before entering the separating channel. This can be achieved using a liquid jet (LJ), a brush—like device, or any other suitable contacting means (FIG. 16a). Using a permeable moving channel element, this wetting action can be promoted by creating a flow through the moving channel element by applying an under pressure at the back-side of the moving element (e.g., using a pump PU1). Microstructured compartments also allow to add the sample which has to analyzed on a sharply delimited, predefined portion of the moving element by simply contacting the fluid in the cups with the sample (FIGS. 16a, b). Similarly, it can also easily be understood that the presence of a system of protrusions and/or upstanding edges on the moving channel element offers the possibility to transport the mobile phase liquid upstream of the channel outlet (e.g., towards a detector D, FIG. 16b) with a minimum of longitudinal dispersion.

For reasons of mechanical strength, the envisioned protrusions should preferably have a width which is of the same order as, or larger than, their height. Flow sustaining protrusions with a smaller width to height ratio will only be preferred when a sufficient mechanical strength can be guaranteed. An increased mechanical strength can be obtained by mechanically linking the protrusions to each other.

An array of protrusions can also be arranged with the sole intention of increasing the rigidity of the moving channel element (e.g., to prevent sagging).

A moving channel element carrying protrusions or compartments which do not extend across the entire channel depth can also be used to transport a fluid (retained in the voids between the protrusions) which is different from the fluid occupying the channel part which is not entered by the protrusions.

One or more protrusions can also be arranged on the wall element carrying the retentive layer. One possible application would be the arrangement of a micro structured array of protrusions (PR) having a substantially uniform height, which can then be used as a reference measure for the thickness of the retentive layer (FIG. 17a). A number of possible variants (looking at the z,x-plane) is given in FIG. 17b. A retentive phase consisting of an array of micro- or nanodevices (for example an array of cylinders or semispheres) can also be considered. This will allow to reduce the retentive phase mass transfer resistance (it is a well known fact that cylinders or spheres have a smaller stationary phase mass transfer resistance than flat geometry). Arranging an array of protrusions in the retentive phase can also be used as a means to support a moving channel element (i.e., when this element carries protrusions which extend over the entire channel depth) during its movement through the channel.

By arranging a microstructure on both the moving and the retentive wall, specific flow patterns (Sf) can be induced which might increase the mobile phase mass transfer rate (FIG. 18a, b). An array of microstructures can also be arranged on the surfaces of the channel elements with the sole intention of reducing the friction resistance and the wear by reducing the contact surface between two given surfaces.

Apart from performing conventional chromatographic separations, the device according to the present invention can also be used to transport one or more different sample species (A, B, . . . ) to one or more distinct and specific zones ($Z_1$, $Z_2$, . . . ) of the retentive layer (FIG. 19a, b) where these species can specifically adsorb or where they may be subjected to a specific chemical, biochemical, photochemical or electrochemical reaction. Considering the very thin (even thinner than 0.1 micrometer) fluid layer which can be transported at very large velocities without creating any significant pressure drop, the devices according to the present invention allow to rapidly analyze highly concentrated samples with a minimum of longitudinal dispersion and with a minimum of time needed for the mass transfer between the fluid phase and the adsorptive or reactive phase. The device is preferentially arranged with detector means which allow to detect the position where the sample species have adsorbed or have reacted. Such detection means can for example be conductivometric, optical, electrical, or of any other suitable nature, and are preferentially arranged in such a way that the position at which the species have adsorbed or reacted can readily be identified. One preferred embodiment involves the use of an optically transparent channel wall element It is also possible to investigate the retentive layer after it has been removed from the analysis device, for example under a microscope. Means can also be included to release the adsorbed species from the separation channel after they have been characterized. These means can be heating or evaporation means, but can also involve the use of solvent elution techniques.

One possible method to introduce the sample to be separated is to create an independent flow in a so-called injection flow channel (IC, FIGS. 20a–c) which is preferably arranged perpendicular to the separating channel (C). The injection flow can be driven by all possible means (electrical, pressure, . . . ), including those described in the present document. Before and after the sample injection process, the injection flow channel is preferably filled with the mobile phase fluid. During the sample injection process, a sharply delimited sample plug (SA) is loaded into the injection channel and is then passed through the injection channel such that the sample material can be contacted with the separating channel fluid. One preferred injection sequence is given in FIG. 20c. In a preferred variant, the moving channel element is put at rest during step II and put into functioning again at the beginning of step III. If desired, the sample fluid can be lead through a number of filters, vessels, recesses, mixers and all other devices required for the sample preparation. Preferentially, the injection channel (IC) is only in contact with the separation channel through a narrow (i.e., in the direction of the separating path) contact zone (injection slit SI, FIG. 20b). This contact zone may be open or may consist of a porous or semi-permeable material. In a preferred variant, the contact zone is a slit made of a suitable material (e.g., elastic) allowing to open and close the slit when desired. The sample material can also be introduced directly into the retentive layer. The contact zone or slit can also be arranged in one of the moving elements.

In another variant, the sample introduction is performed using a movably arranged vessel or container divided into two separated compartments (FIGS. 20a, c) Shifting this device back and forth, an equivalent of the injection sequence presented in FIG. 20a, c) is obtained. The actual injection occurs during step IT. Preferentially, the container part containing the mobile phase fluid is larger than the part containing the sample liquid and is arranged with a mixing device (Im).

If desired, the wall carrying the retentive layer can be arranged between a pre- and a post-channel part. These parts can have a channel recess with a cross section which can differ from the cross-section of the actual separation channel. The pre- and post-channel parts can for example be used for post or pre-column splitting or can be used to accommodate the injection and detection means. Alignment of the side banks of the pre and post-channel parts with the side-banks of the actual separating channel can simply be arranged by pushing all parts against the moving wall.

Figure 23A:
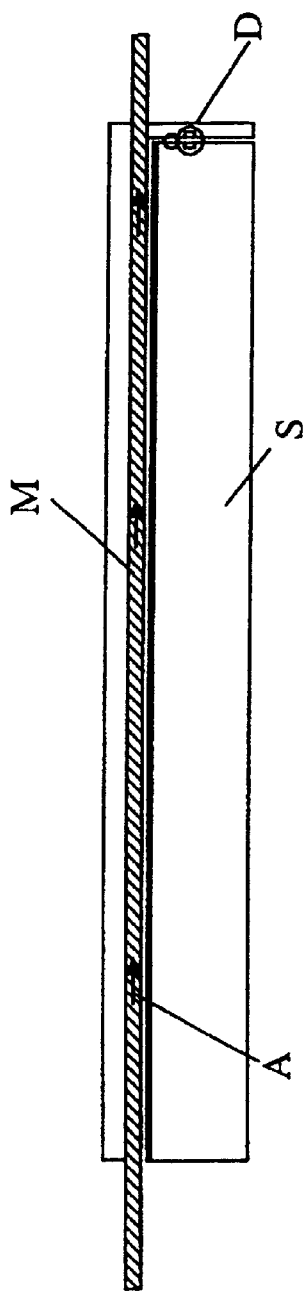
FIGS. 23. (a, b). detection in side-channel machined in stationary element.
Figure 23B:
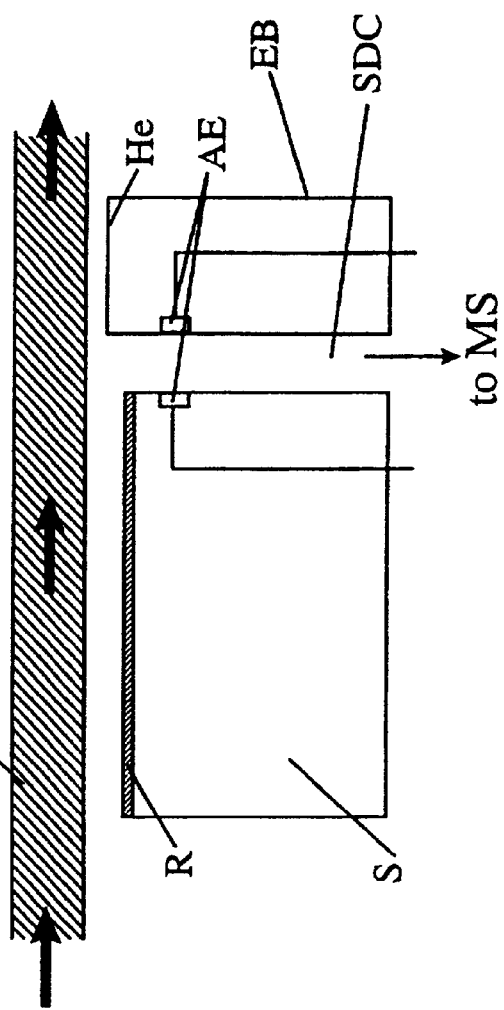

The separating device according to the present invention allows the use of all detection means and detection schemes presently used in liquid or gas phase chromatography and in capillary electrophoresis. On column detection schemes (in which the sensing elements of the detector are integrated in the separation channel) can be considered as well as off-column detection schemes. FIGS. 22a–23b show a number of possible on detection schemes. The possibility to use a divergent end-section (TE) is suggested in FIG. 22b. As indicated, the active detection elements (AE) can be arranged in the side-walls as well as in the stationary wall. Using a transparent channel wall element (e.g., a moving polymer wall or a stationary glass-like wall), the detection might also occur through this wall element, for example by means of a microscope. The detection can also occur in (or upstream of) a side channel (SDC) arranged in the stationary channel wall (FIGS. 23a, b). If desired, a flow can be created in this channel using any type of force field, including electrical, centrifugal, gravitational, pressure or suction force and even a capillary force. It should be noted that the end-block (EB) of the stationary wall may also substantially touch the moving element or may be limited to any other suitable level. The detection channel can also be used to guide the fluid to a mass spectrometer.

Preferably, the detection and injection devices, the solvent in- and outlet systems, the solvent vessel and the driving devices for the moving channel elements are all grouped in one block, whereas the retentive phase is arranged on a separate, easily removable plate or other suitable device. Considering furthermore that no high pressure fittings between column and other parts are needed, it is obvious that the retentive phase can be very easily replaced, allowing the separating device to combine an on-column detection scheme with the same operational flexibility (cfr. column replacement) as conventional capillary GC and HPLC. To operate the separating device under sub- or supra-atmospheric conditions channel conditions, the entire envelope of the device should preferably be sealed, such that the pressure within this envelope can be put at the desired channel pressure.

Figure 24:
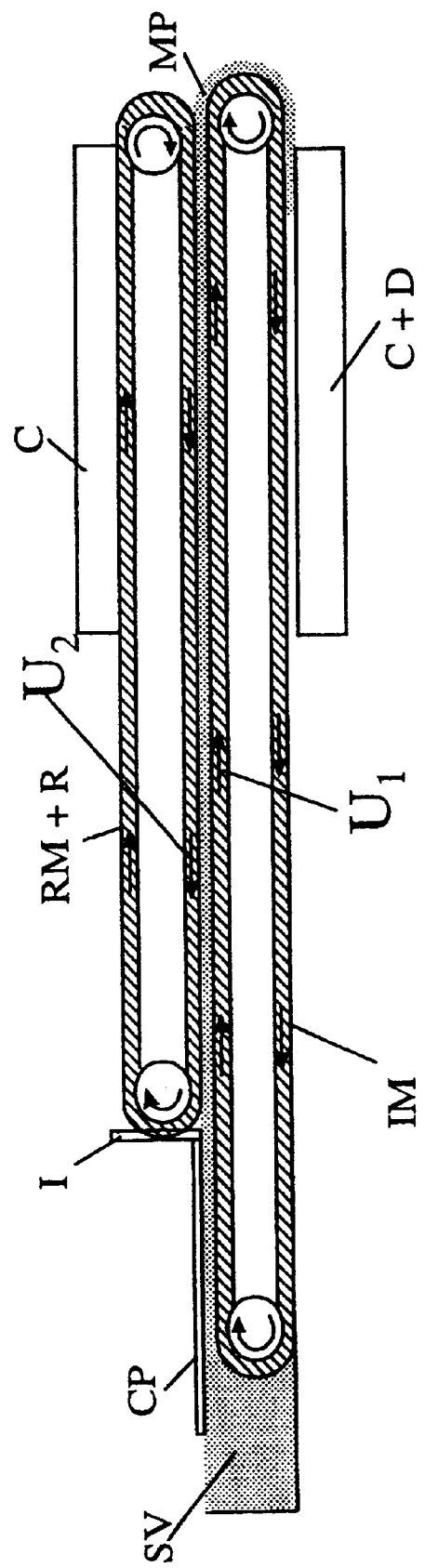
FIG. 24. a dual Opposite-Moving-Channel-Elements system.
Figure 25A:
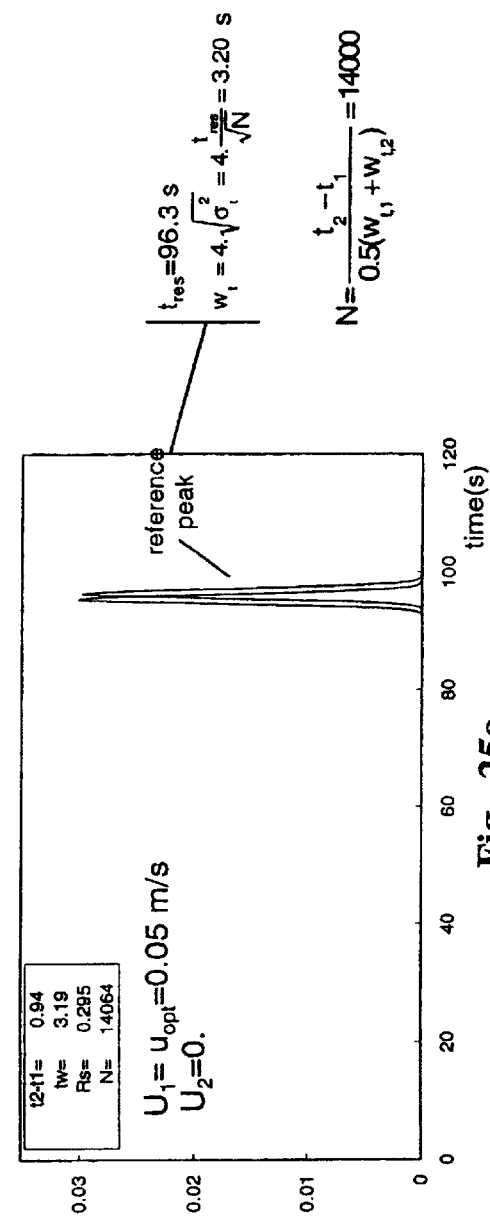
FIGS. 25. (a, b). difference in critical pair separation efficiency between a stationary and an opposite-moving retentive layer.
Figure 25B:
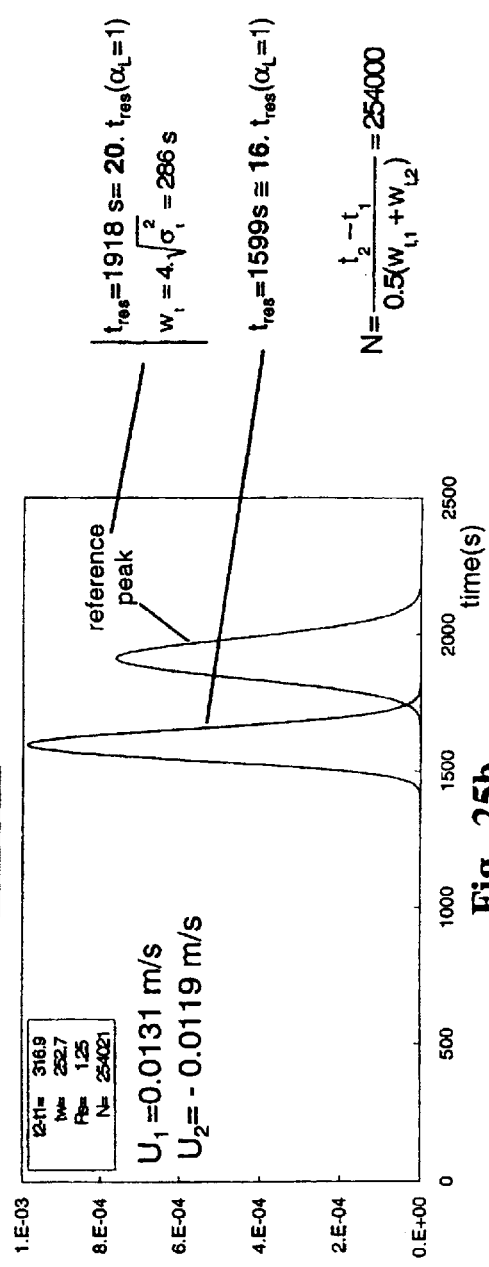
Figure 26:
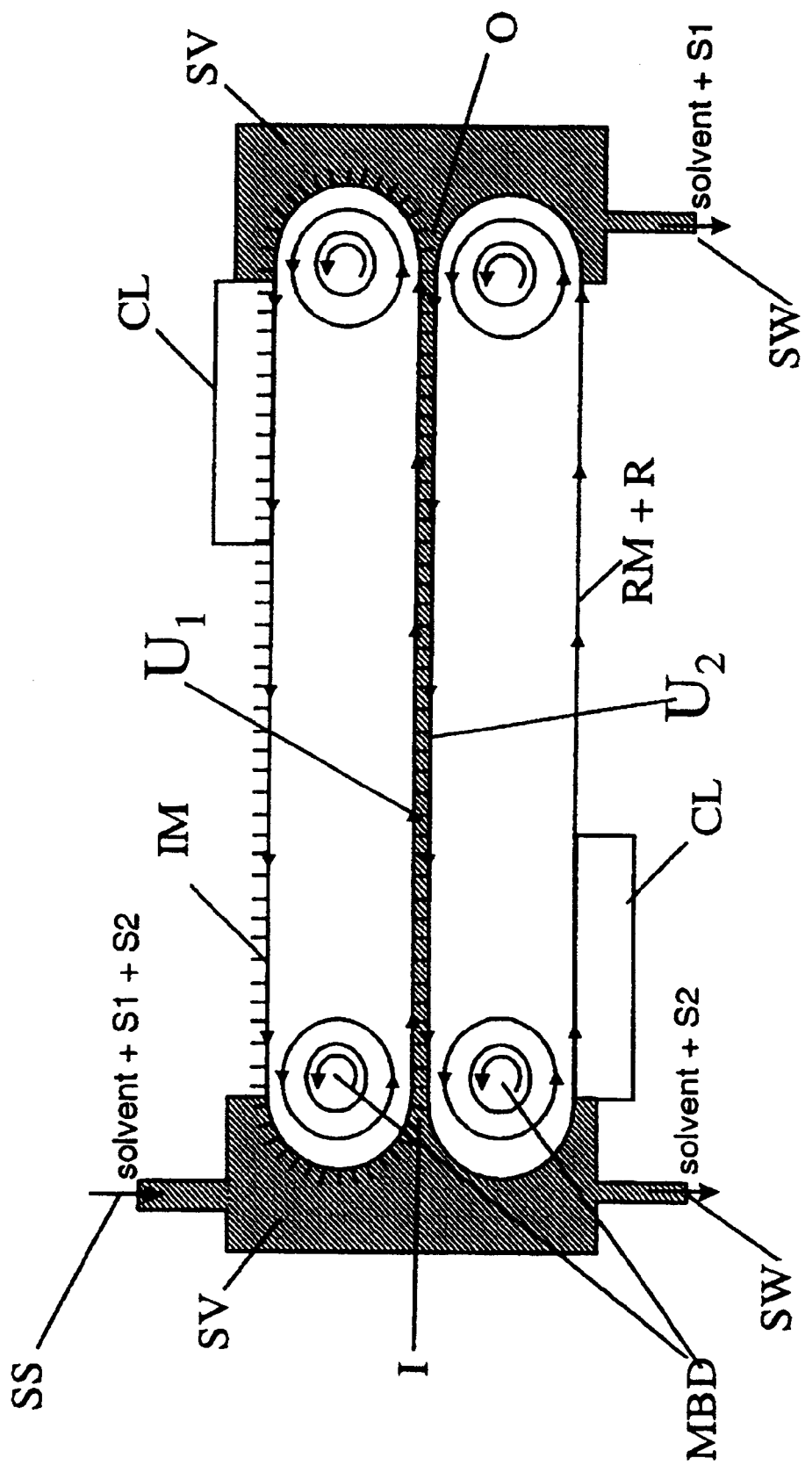
FIG. 26. a dual Opposite-Moving-Channel-Elements system, adapted to perform continuous chromatographic separation.

In some especially preferred embodiments according to the present invention (the so-called Opposite-Moving-Channel-Elements system), the retentive phase is subjected to a relative motion with respect to the detection point, while keeping the detection point fixed in space. A possible embodiment which allows to combine two opposite moving channel elements with a fixed detection point is based upon the use of a double moving-belt system based (FIG. 24). One moving channel element (IM) determines the direction of the mobile phase flow, whereas the other moving channel element (RM) carries the retentive phase (R) and moves in the opposite direction. In the device according to the present invention, the relative velocity between the retentive and inert channel elements can be selected such that it is equal to the optimal velocity (i.e., the velocity yielding the minimal theoretical plate height) of the system where the retentive wall is at rest. In this way, the moving retentive wall system has the same local theoretical plate height as the stationary retentive wall system. After deciding on the relative velocity difference, the absolute (negative) velocity of the retentive channel element (U2) can still be selected independently. This velocity can then be selected such that even the sample species with the largest affinity still have a net positive velocity (i.e., they move from injection to detection point) while their residence time in the separation channel is strongly increased (retentive channel elements move slower than inert channel elements). As a consequence, the number of theoretical plates (and the separation quality) which can be achieved in a given column length is drastically increased compared to the case in which the retentive phase is at rest. To be sure that every component will pass the detector, the calculation of the velocities of the moving channel elements should be based upon the column retention factor of the last eluting component. In the simulated example given in FIGS. 25,a, b the velocities U1 and U2 are selected such that the residence time of the last eluting peak (reference peak) is increased by a factor 20. In a preferred embodiment (see FIG. 24), the inert element (IM) is used to transport the sample solutes towards a mass spectrometer (D), or any other suitable detection device, positioned at a given distance upstream of the separation channel. Cleaning devices (CL) for the moving channel elements should preferentially be provided. In a special variant of the method shown in FIG. 24, the velocities of the inert (MI) and the retentive moving channel element (MR) are selected such that part of the sample solute species (S1) moves in the same direction as the mobile phase, whereas the other part of the sample solute species (S2) moves in the opposite direction. Such a device (schematically represented in FIG. 26), equipped with means for continuous sample supply (SS) and continuous withdrawal (SW) of separated substances, is excellently suited to perform continuous chromatographic separations. To ensure an optimal operation, moving column part cleaning or regeneration devices (CL) have to be provided.

What is claimed is:

1. Method for separating components of a sample for identification thereof comprising contacting the sample with a mobile phase fluid and transporting the mobile phase fluid through a separation channel having two ends and having at least one retentive layer arranged therein;

further comprising transporting the mobile phase fluid in only one flow direction, in one end of the separation channel, through the separation channel, and out of the other end of the separation channel, the separation channel being open during separation of the components;

wherein the separation channel comprises at least two channel elements, wherein one channel element is a moving channel element, the moving channel element continuously transporting the mobile phase fluid;

wherein each sample component has a different residence time in the separation channel or has a unique position at which it is retained in the separation channel; and further comprising separating the sample components utilizing the different residence time or the unique position of each component in the separation channel.

2. Method according to claim 1 further comprising sustaining the flow of the mobile phase fluid and the sample through the separation channel by relief elements arranged on at least one of the channel elements.

3. Method according to claim 2 further comprising selecting a motion velocity of the moving channel element to effect a continuous separation.

4. Method according to claim 2 further comprising applying an additional force to transport the mobile phase.

5. Method according to claim 2 wherein the mobile phase is a liquid, a gas, or a super-critical fluid.

6. Method according to claim 1 further comprising transporting the mobile phase fluid and the sample through the separation channel by a system of substantially non-intermixing compartments arranged on the moving channel element.

7. Method according to claim 6 further comprising promoting mixing inside the compartments.

8. Method according to claims 1 further comprising increasing the residence time of the sample in the separation channel by moving the retentive layer and the mobile phase with respect to a detection point in a mutually opposite direction.

9. Method according to claim 1 further comprising varying the composition of the mobile phase fluid during the separation.

10. Method according to claim 1 further comprising varying the channel temperature during the separation.

11. Method according to claim 1 further comprising imposing one or more spatial temperature gradients within the separation channel.

12. Method according to claim 1 further comprising subjecting the sample components to a chemical or physical reaction at a position inside the separation channel.

13. A device for identifying components of a sample, said device comprising a separation channel in which at least one retentive layer is arranged to allow a mobile phase comprising an injected sample and a carrier fluid to progress through the channel and to separate the sample into its components;
wherein each sample component has a different residence time in said separation channel or a unique position at which it is retained in said separation channel such that the sample components are separated by their different residence time or unique position;
the device further comprises means for transporting the mobile phase in one progressive flow direction in, through and out of the separation channel;
wherein the separation channel is an open channel having only one inlet at a first end and one outlet at a second end, wherein the separation channel is defined by at least two channel elements wherein one of the channel elements is a first movable channel element;
wherein the means for transporting the mobile phase comprises the first movable channel element, wherein the first movable channel element transports the mobile phase in only one progressive flow direction from the channel inlet into said separation channel, through said separation channel, and out of said separation channel though the outlet; the first movable channel element being slidably arranged substantially parallel to the other channel element(s).

14. Device according to claim 13 wherein a part of the first movable channel element is slidably arranged outside of the separation channel.

15. Device according to claim 13 wherein at least part of the separation channel is recessed into the first movable channel element.

16. Device according to claim wherein at least one or more relief elements are arranged on at least one of the channel elements.

17. Device according to claim 16 wherein the relief elements substantially extend over the entire channel depth.

18. Device according to claim 13 wherein a system of substantially non-intermixing compartments is arranged on the first movable channel element.

19. Device according to claim 15 wherein mixing means are provided in the compartments to promote mass transfer inside the compartments.

20. Device according to claim 13 comprising two slidably arranged channel elements, the elements being movable in the separation channel in a mutual opposite axial direction.

21. Device according to claim 13 further comprising means for removing, deactivating, or diluting the sample after moving out of the separation channel or past a detection point.

22. Device according to claim 13 wherein at least part of the at least one retentive layer comprises a material displaying a gradual or discrete chemical or physical variation, and the device further comprising detection means to detect the position and quantity of the separated components.

23. Device according to claim 13 wherein comprising one or more means for heating or cooling the separation channel integrated in at least one of the channel elements, in at least one of the retentive layers, or both.

24. Device according to claim 13 wherein comprising guiding and tensioning means for determining the parallel position of the slidably arranged channel element in the separation channel and means to control the tension applied to the slidably arranged channel element.

25. Device according to claim 13 wherein at least one of the surfaces of the first movable channel element is contacted with the mobile phase by creating a flow perpendicular to and through the first movable channel element.

26. Device according to claim 13 wherein comprising means to set the pressure inside the channel.

27. Device according to claim 13 wherein the separation channel has a circular, semi-circular, ellipsoidal, square or rectangular cross-sectional.

28. Device according to claim 13 wherein the separation channel is arranged on a substantially planar surface or on a non-planar surface.

29. Device according to claim 13 wherein the first movable channel element is connected to a motor device or is linked to a moving surface.

30. Device according to claim 29 wherein the moving surface is a transport belt.

31. Device according to claim 13 wherein all of the channel elements are sufficiently flexible to allow the separation channel to be wound at least once around a mechanical object.

32. Device according to claim 13 wherein the retentive layer comprises a micro-structured array of cylinders or semi-spheres.

33. Device according to claim 13 wherein comprising an adsorptive, absorptive, reactive or porous layer arranged on the first movable channel element.

34. Device according to claim 13 wherein comprising a detection device at the end of the separation channel.

* * * * *

UNITED STATES PATENT AND TRADEMARK OFFICE
CERTIFICATE OF CORRECTION

PATENT NO.    : 6,565,752 B1                                                                Page 1 of 1
DATED         : May 20, 2003
INVENTOR(S)   : Gino Baron et al.

It is certified that error appears in the above-identified patent and that said Letters Patent is hereby corrected as shown below:

Column 20,
Line 4, -- 13 -- has been added before "wherein";
Line 12, "15" has been replaced with -- 18 --;
Lines 27, 31, 40, 60 and 63, "wherein" has been replaced with -- further --.

Signed and Sealed this

Twenty-eighth Day of October, 2003

JAMES E. ROGAN
*Director of the United States Patent and Trademark Office*